(12) United States Patent
Lindsey et al.

(10) Patent No.: US 7,470,785 B2
(45) Date of Patent: Dec. 30, 2008

(54) REFINED ROUTES TO CHLORIN BUILDING BLOCKS

(75) Inventors: Jonathan S. Lindsey, Raleigh, NC (US); Masahiko Taniguchi, Raleigh, NC (US); Doyoung Ra, Taejon (KR); Guoning Mo, Ontario (CA); Thiagarajan Balasubramanian, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 525 days.

(21) Appl. No.: 11/072,196

(22) Filed: Mar. 4, 2005

(65) Prior Publication Data

US 2005/0165228 A1    Jul. 28, 2005

Related U.S. Application Data

(62) Division of application No. 10/140,654, filed on May 8, 2002, now Pat. No. 6,946,552.

(60) Provisional application No. 60/289,985, filed on May 10, 2001.

(51) Int. Cl.
   *C07B 47/00*  (2006.01)
(52) U.S. Cl. ...................... 540/145
(58) Field of Classification Search ............... 540/145
   See application file for complete search history.

(56) References Cited

U.S. PATENT DOCUMENTS 5,225,433 A    7/1993   Dougherty et al.

OTHER PUBLICATIONS

International Search Report for International Application Ser. NO. PCT/US02/14503 dated Aug. 7, 2002.
Taniguchi et al., *Chemical Abstracts* 136:30780 (2001).

*Primary Examiner*—James O. Wilson
*Assistant Examiner*—Paul V. Ward
(74) *Attorney, Agent, or Firm*—Myers Bigel Sibley & Sajovec, P.A.

(57) ABSTRACT

A method of making chlorins comprises the steps of reacting (e.g. condensing) a dipyrrin western half intermediate with an eastern half intermediate to form a tetrahydrobilene, and then cyclizing the tetrahydrobilene to form a chlorin. Intermediates including tetrahydrobilenes useful in such reactions are also described.

6 Claims, 4 Drawing Sheets

REFINED ROUTES TO CHLORIN BUILDING BLOCKS

CLAIM FOR PRIORITY AND CROSS-REFERENCE TO OTHER APPLICATIONS

This application claims priority to and is a divisional of parent application Ser. No. 10/140,654 filed May 8, 2002, now U.S. Pat. No. 6,946,552 which claims priority to U.S. provisional application No. 60/289,985, filed May 10, 2001, the disclosure of which is hereby incorporated herein by reference.

RELATED APPLICATIONS

This application claims the benefit of Provisional Application Ser. No. 60/289,985, filed May 10, 2001, the disclosure of which is incorporated by reference herein in its entirety.

STATEMENT OF FEDERAL SUPPORT

This invention was made with Government support under Grant No. GM36238 from the National Institutes of Health. The Government has certain rights to this invention.

FIELD OF THE INVENTION

The present invention concerns methods and intermediates useful for the synthesis of chlorins.

BACKGROUND OF THE INVENTION

A synthetic route that provides access to chlorin building blocks bearing substituents at the meso- and/or β-positions has recently been described (Strachan, et al. (2000) *J. Org. Chem.* 65:3160-3172; Balasubramanian, et al. (2000) *J. Org. Chem.* 65:7919-7929). In addition to selected patterns of functional group handles at the perimeter of the macrocycle, each chlorin bears a geminal dimethyl group to lock in the hydrogenation level yet lacks steric congestion or other unwanted functionality around the reduced ring. The synthesis involves the construction of an Eastern half and a Western half, which are joined to form the chlorin macrocycle in the final step (Scheme 1). This convergent coupling of the Eastern half and Western half is performed in a two-flask procedure involving acid-catalyzed condensation to give a dihydrobilene-α, followed by metal-mediated oxidative cyclization to give the chlorin. The Eastern half, a bromodipyrromethane-monocarbinol, is readily available by the acylation and bromination of a dipyrromethane at the 1- and 9-positions, respectively, followed by reduction. The Western half is a dihydrodipyrrin (1). The Western half has limited stability and generally must be prepared from the stable nitro-hexanone pyrrole precursor and used within a few days.

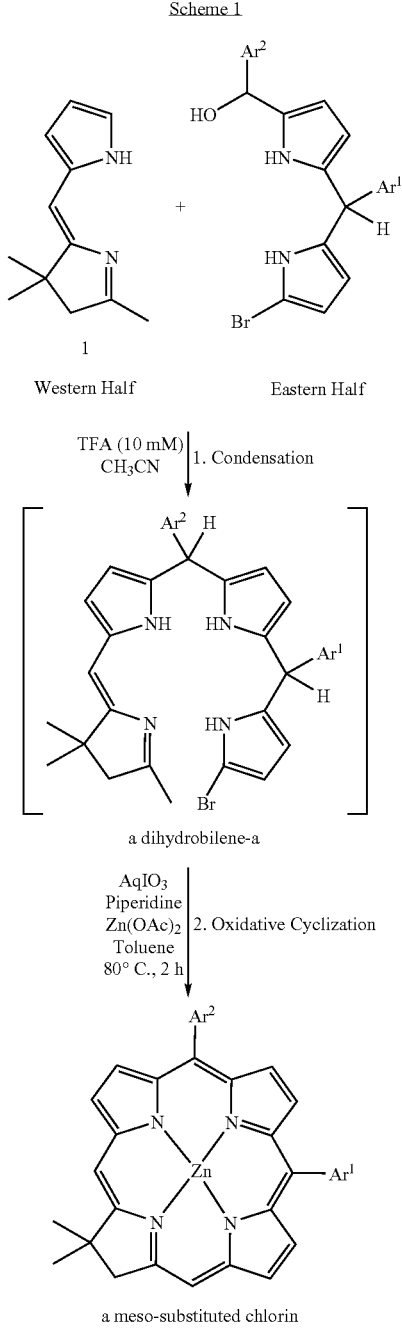

In our initial search for routes to a suitable Western half, we investigated the synthesis of a tetrahydrodipyrrin via an intermediate tetrahydrodipyrrin N-oxide (comprised of a pyrrole and a pyrroline N-oxide)(Strachan, et al. (2000) *J. Org. Chem.* 65:3160-3172). The formation of N-oxides by cyclization followed by deoxygenation affords a convenient entry to a number of heterocycles (Katritzky and Lagowski, *Chemistry of the Heterocyclic N-Oxides*, Academic Press: London and New York, 1971, pp. 166-231; Ochiai, E. *Aromatic Amine Oxides*, Elsevier: Amsterdam, 1967, pp. 184-209; Albini, A.; Pietra, S. *Heterocyclic N-Oxides*, CRC Press: Boca Raton, 1991, pp. 120-134). Indeed, pyrroline N-oxides played a central role throughout Todd's studies related to the synthesis of vitamin B$_{12}$ (Bonnett, et al. (1959) *J. Chem. Soc.* 2094-2102; Bonnett et al. (1959) *J. Chem. Soc.* 2102-2104; Bonnett, et al. (1959) *J. Chem. Soc.* 2105-2108; Brown et al. (1959) *J. Chem. Soc.* 2109-2116; Brown et al. (1959) *J. Chem. Soc.* 2116-2122; Clark, et al. (1959) *J. Chem. Soc.* 2123-2127; Bowering et al. (1963) *Annalen* 669:106-113; Brown, et al. (1965) *J. Chem. Soc.* 2337-2340; Brown et al. (1966) *Tetrahedron, Suppl.* 8, Part 1:15-26; Black, et al. (1976) *J. Chem. Soc. Perkin Trans. I* (18):1942-1943; Black, et al. (1976) *J. Chem. Soc. Perkin Trans. I* (18):1944-1950; Black, et al. (1976) *J. Chem. Soc. Perkin Trans. I* (18):1951-1954; Alderson et al. (1976) *J. Chem. Soc. Perkin Trans. I* (18):1955-1960). Battersby synthesized a tetrahydrodipyrrin N-oxide, converted it to the corresponding tetrahydrodipyrrin, and upon reaction with a 1-bromo-9-bromomethyldipyrrin in the presence of copper acetate obtained the copper chlorin in 6.9% yield (2.8 mg) (Battersby, et al. (1984) *J. Chem. Soc. Perkin Trans. I* (12):2725-2732). Though Battersby's pyrrole component was substituted with one ester and two alkyl groups, the route employed also proved suitable for our synthesis of a tetrahydrodipyrrin N-oxide incorporating an unsubstituted pyrrole unit (Strachan, et al. (2000) *J. Org. Chem.* 65:3160-3172). Thus, cyclization of a nitro-hexanone pyrrole (2) afforded the corresponding tetrahydrodipyrrin N-oxide (3), but we were unable to, deoxygenate the cyclic nitrone and form the tetrahydrodipyrrin Western half (4) (Strachan, et al. (2000) *J. Org. Chem.* 65:3160-3172). We resorted to the cyclization of the nitro-hexanone pyrrole 2 with NaOMe/THF followed by TiCl$_3$ in NH$_4$OAc-buffered solution, forming the dihydrodipyrrin 1 directly (without isolating the N-oxide) in yields of 20-30% (Strachan, et al. (2000) *J. Org. Chem.* 65:3160-3172; Balasubramanian, et al. (2000) *J. Org. Chem.* 65:7919-7929).

SUMMARY OF THE INVENTION

A first aspect of the present invention is a method of making a chlorin of Formula X:

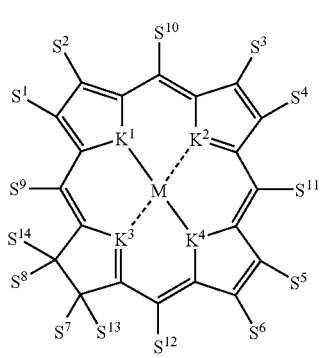

wherein:

M is a metal, such as a metal selected from the group consisting of Cu, Zn, Mg, Pt, Pd, Sn and Al, or M is absent;

$K^1$, $K^2$ and $K^4$ are independently selected atoms, such as atoms or hetero atoms independently selected from the group consisting of N, O, S, Se, Te, and CH (preferably not CH, and most preferably N);

$K^3$ is N;

$S^1$, $S^2$, $S^3$, $S^4$ $S^5$, $S^6$, $S^7$, $S^8$, $S^9$, $S^{10}$, $S^{11}$, $S^{12}$, $S^{13}$, and $S^{14}$ are independently selected substituents, such as substituents selected from the group consisting of H, aryl, phenyl, cycloalkyl, alkyl, alkenyl, alkynyl, halogen, alkoxy, alkylthio, perfluoroalkyl, perfluoroaryl, pyridyl, cyano, thiocyanato, nitro, amino, alkylamino, acyl, sulfoxyl, sulfonyl, imido, amido, and carbamoyl (e.g., H or alkyl). Preferably at least $S^8$ and $S^{14}$ are both not H (e.g., both are alkyl). In addition, from one to four of $S^1$, $S^2$, $S^3$, $S^4$ $S^5$, $S^6$, $S^7$, $S^8$, $S^9$, $S^{10}$, $S^{11}$, $S^{12}$, $S^{13}$, and $S^{14}$ may optionally be independently selected linking groups Q, such as linking groups Q are of the formula:

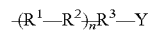

wherein:

n is from 0 or 1 to 5 or 10;

$R^3$ may be present or absent;

$R^1$, $R^2$, and $R^3$ are each independently selected from the group consisting of ethene, ethyne, aryl, and heteroaryl groups, which aryl and heteroaryl groups may be unsubstituted or substituted one or more times with H, aryl, phenyl, cycloalkyl, alkyl, alkenyl, alkynyl, halogen, alkoxy, alkylthio, perfluoroalkyl, perfluoroaryl, pyridyl, cyano, thiocyanato, nitro, amino, alkylamino, acyl, sulfoxyl, sulfonyl, imido, amido, and carbamoyl; and Y is a protected or unprotected reactive substituent, such as a reactive substituent selected from the group consisting of hydroxy, thio, seleno, telluro, ester, carboxylic acid, boronic acid, phenol, silane, sulfonic acid, phosphonic acid, alkylthiol, formyl, halo, alkenyl, alkynyl, haloalkyl, alkyl phosphonate, alkyl sulfonate, alkyl carboxylate, and alkyl boronate groups.

The method comprises oxidatively cyclizing a tetrahydrobilene of Formula XI:

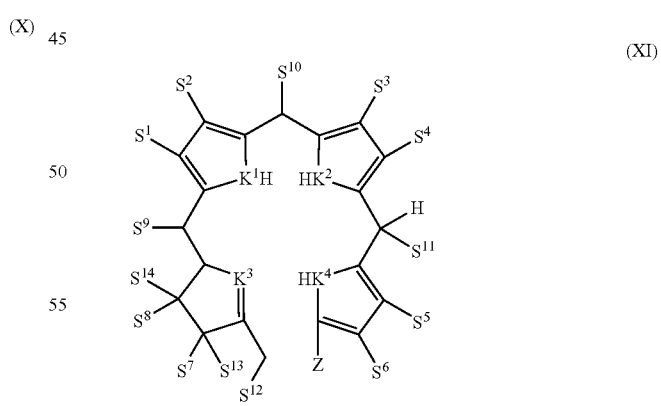

wherein Z is selected from the group consisting of halo, alkoxy, and acyloxy (preferably in an organic solvent in the presence of a base, an oxidant and a metal salt MX$_n$, where X is an anion, and n is 2-3, to produce a compound of Formula X above), and then optionally displacing metal M to create a free base chlorin.

A second aspect of the present invention is a method of making a tetrahydrobilene of Formula XI:

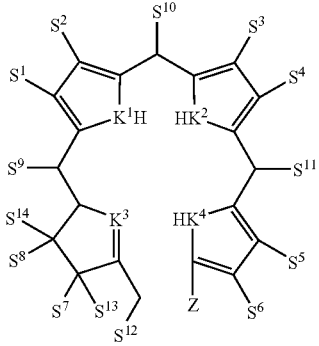

(XI)

wherein: $K^1$, $K^2$ $K^3$ and $K^4$ are as described above; $S^1$, $S^2$, $S^3$, $S^4$ $S^5$, $S^6$, $S^7$, $S^8$, $S^9$, $S^{10}$, $S^{11}$, $S^{12}$, $S^{13}$, and $S^{14}$ are as described above; and Z is as described above. The method comprising condensing a compound of Formula WH with a compound of Formula EH

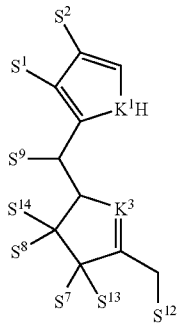

WH

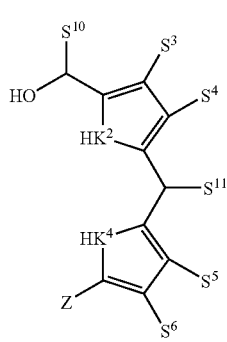

EH (preferably in an organic solvent in the presence of an acid) to form a tetrahydrobilene of Formula XI.

A third aspect of the present invention is a tetrahydrobilene of Formula XI:

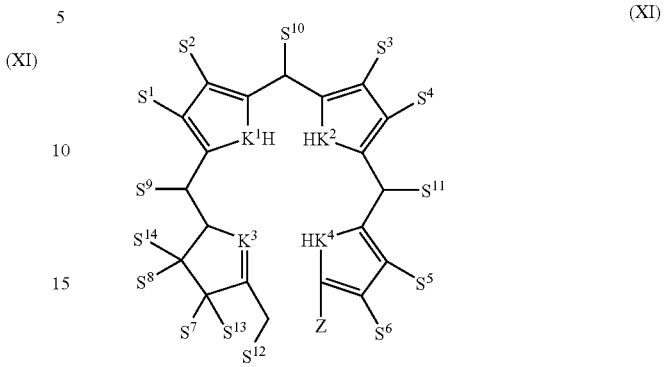

(XI)

wherein: $K^1$, $K^2$ $K^3$ and $K^4$ are as described above; $S^1$, $S^2$, $S^3$, $S^4$ $S^5$, $S^6$, $S^7$, $S^8$, $S^9$, $S^{10}$, $S^{11}$, $S^{12}$, $S^{13}$, and $S^{14}$ are as described above; and Z is as described above.

A fourth aspect of the present invention is a compound of Formula WH:

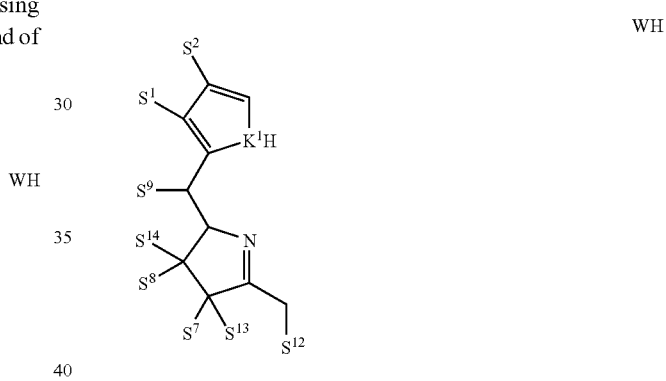

WH wherein:
$K^1$ is as described above; and $S^1$, $S^2$, $S^7$, $S^8$, $S^9$, $S^{12}$, $S^{13}$, and $S^{14}$ are as described above (preferably subject to the proviso that $S^1$ and $S^2$ are not simultaneously alkyl).

A fifth aspect of the present invention is a method of making a compound of Formula WH:

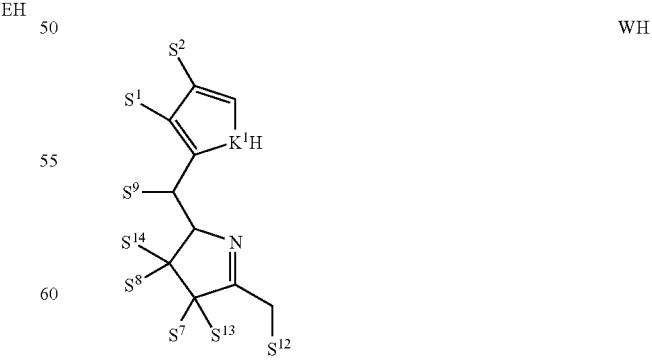

WH wherein: $K^1$ is as given above, $S^1$, $S^2$, $S^7$, $S^8$, $S^9$, $S^{12}$, $S^{13}$, and $S^{14}$ are as given above (not necessarily subject to the proviso noted immediately above).

The method comprises reacting a compound of Formula III

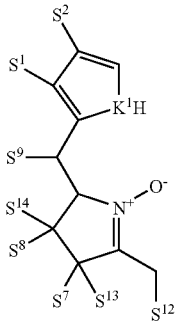

in an organic solvent (preferably in the presence of Ti(0)) to form the compound of Formula WH.

A sixth aspect of the present invention is a compound according to Formula III:

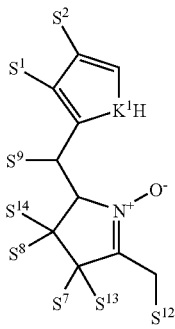

wherein: $K^1$ is as given above; and $S^1$, $S^2$, $S^7$, $S^8$, $S^9$, $S^{12}$, $S^{13}$, and $S^{14}$ are as given above (preferably subject to the proviso that $S^1$ and $S^2$ are not simultaneously alkyl).

A seventh aspect of the present invention is a method of making a compound of Formula III:

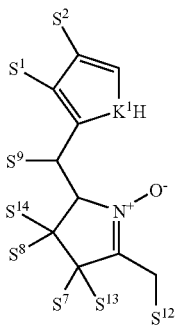

wherein: $K^1$ is as given above, and $S^1$, $S^2$, $S^7$, $S^8$, $S^9$, $S^{12}$, $S^{13}$, and $S^{14}$ are as given above. The method comprises cyclizing a compound of Formula II:

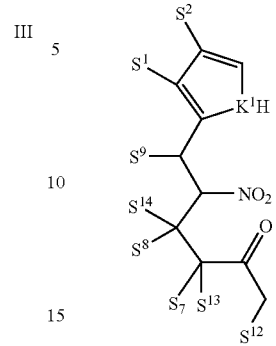

(preferably in an organic solvent under reducing conditions, for example in the presence of zinc oxid and acetic acid) to produce a compound of Formula III.

An eighth aspect of the present invention is a compound of Formula II:

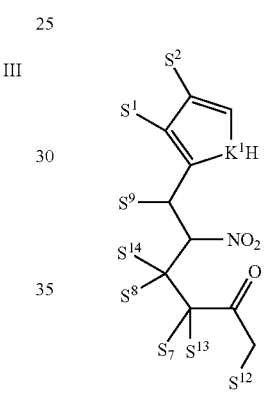

wherein $K^1$ is as given above, and $S^1$, $S^2$, $S^7$, $S^8$, $S^9$, $S^{12}$, $S^{13}$, and $S^{14}$ are as given above.

A ninth aspect of the present invention is a compound of Formula X:

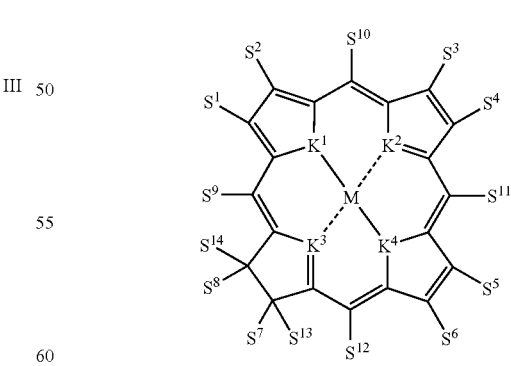

wherein:
M is as given above,
$K^1$, $K^2$ $K^3$ and $K^4$ are as given above;
$S^1$, $S^2$, $S^3$, $S^4$ $S^5$, $S^6$, $S^8$, $S^9$, $S^{10}$, $S^{11}$, $S^{12}$, and $S^{14}$ are as given above;

$S^7$ and $S^{13}$ are together =O; and from one to four of $S^1$, $S^2$, $S^3$, $S^4$ $S^5$, $S^6$, $S^8$, $S^9$, $S^{10}$, $S^{11}$, $S^{12}$, and $S^{14}$ are independently selected linking groups Q as given above. In a particular embodiment at least $S^1$ is a linking group Q, and in a paraticular embodiment $S^1$ is a halogen such as iodo.

The foregoing and other objects and aspects of the present invention are explained in greater detail in the drawings herein and the specification set forth below.

DETAILED DESCRIPTION OF PREFERRED EMBODIMENTS

Figure 1:
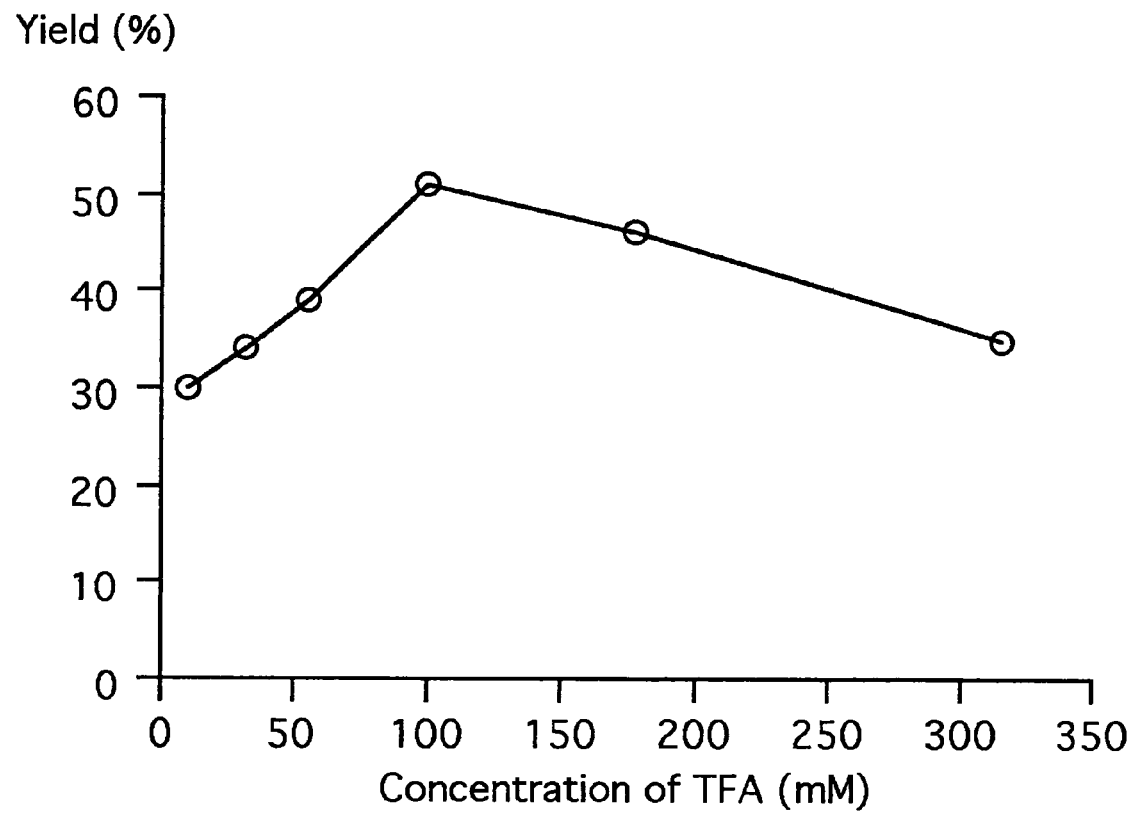
FIG. 1 shows the effect of the concentration of TFA on the condensation of Eastern half (6a-OH) and Western half (4). The yield shown refers to the amount of chlorin formed upon treatment of the crude product to the oxidation conditions (analogous to a one-flask reaction) followed by UV-Vis spectroscopy.

The term "substituent" as used in the formulas herein, particularly designated by S or S" where n is an integer, in a preferred embodiment refer to electron-rich or electron-deficient groups (subunits) that can be used to adjust the redox potential(s) and/or spatial properties of the subject compound. Preferred substituents include, but are not limited to, H, aryl, phenyl, cycloalkyl, alkyl, alkenyl, alkynyl, halogen, alkoxy, alkylthio, perfluoroalkyl, perfluoroaryl, pyridyl, cyano, thiocyanato, nitro, amino, alkylamino, acyl, sulfoxyl, sulfonyl, amido, and carbamoyl. In certain embodiments, a substituted aryl group is attached to a porphyrin or a porphyrinic macrocycle, and the substituents on the aryl group are selected from the group consisting of aryl, phenyl, cycloalkyl, alkyl, alkenyl, alkynyl, halogen, alkoxy, alkylthio, perfluoroalkyl, perfluoroaryl, pyridyl, cyano, thiocyanato, nitro, amino, alkylamino, acyl, sulfoxyl, sulfonyl, amido, and carbamoyl. Additional substituents include, but are not limited to, 4-chlorophenyl, 4-trifluoromethylphenyl, and 4-methoxyphenyl. Preferred substituents provide a redox potential range of less than about 5 volts, preferably less than about 2 volts, more preferably less than about 1 volt.

The term "aryl" refers to a compound whose molecules have the ring structure characteristic of benzene, naphthalene, phenanthrene, anthracene, etc. (i.e., either the 6-carbon ring of benzene or the condensed 6-carbon rings of the other aromatic derivatives). For example, an aryl group may be phenyl ($C_6H_5$) or naphthyl ($C_{10}H_7$). It is recognized that the aryl group, while acting as substituent can itself have additional substituents (e.g. the substituents provided for S" in the various formulas herein).

The term "alkyl" refers to a paraffinic hydrocarbon group, typically C1 to C4, which may be derived from an alkane by dropping one hydrogen from the formula. Examples are methyl ($CH_3$—), ethyl ($C_2H_5$—), propyl ($CH_3CH_2CH_2$—), isopropyl (($CH_3)_2CH$—).

The term "alkenyl" refers to a hydrocarbon group, typically C2 to C4, derived from the corresponding alkyl and which contains at least one double bond (e.g., butadienyl).

The term "alkynyl" refers to a hydrocarbon group, typically C2 to C4, derived from the corresponding alkyl and which contains at least one triple bond (e.g., butadienyl).

The term "halogen" refers to one of the electronegative elements of group VIIA of the periodic table (fluorine, chlorine, bromine, iodine, astatine).

The term "perfluoroalkyl" refers to an alkyl group where every hydrogen atom is replaced with a fluorine atom.

The term "perfluoroaryl" refers to an aryl group where every hydrogen atom is replaced with a fluorine atom.

The term "pyridyl" refers to an aryl group where one CR unit is replaced with a nitrogen atom.

The term "sulfoxyl" refers to a group of composition RS(O)— where R is some alkyl, aryl, cycloalkyl, perfluoroalkyl, or perfluoroaryl group. Examples include, but are not limited to methylsulfoxyl, phenylsulfoxyl, etc.

The term "sulfonyl" refers to a group of composition $RSO_2$— where R is some alkyl, aryl, cycloalkyl, perfluoroalkyl, or perfluoroaryl group. Examples include, but are not limited to methylsulfonyl, phenylsulfonyl, p-toluenesulfonyl, etc.

The term "carbamoyl" refers to the group of composition $R^1(R^2)NC(O)$— where $R^1$ and $R^2$ are H or some alkyl, aryl, cycloalkyl, perfluoroalkyl, or perfluoroaryl group. Examples include, but are not limited to N-ethylcarbamoyl, N,N-dimethylcarbamoyl, etc.

The term "amido" refers to the group of composition $R^1CON(R^2)$— where $R^1$ and $R^2$ are H or some alkyl, aryl, cycloalkyl, perfluoroalkyl, or perfluoroaryl group. Examples include, but are not limited to acetamido, N-ethylbenzamido, etc.

The term "acyl" refers to an organic acid group in which the —OH of the carboxyl group is replaced by some other substituent (RCO—). Examples include, but are not limited to acetyl, benzoyl, etc.

In preferred embodiments, when a metal is designated by "M" or "M"", where n is an integer, it is recognized that the metal may be associated with a counterion.

As noted above, the present invention provides a method of making a chlorin of Formula X:

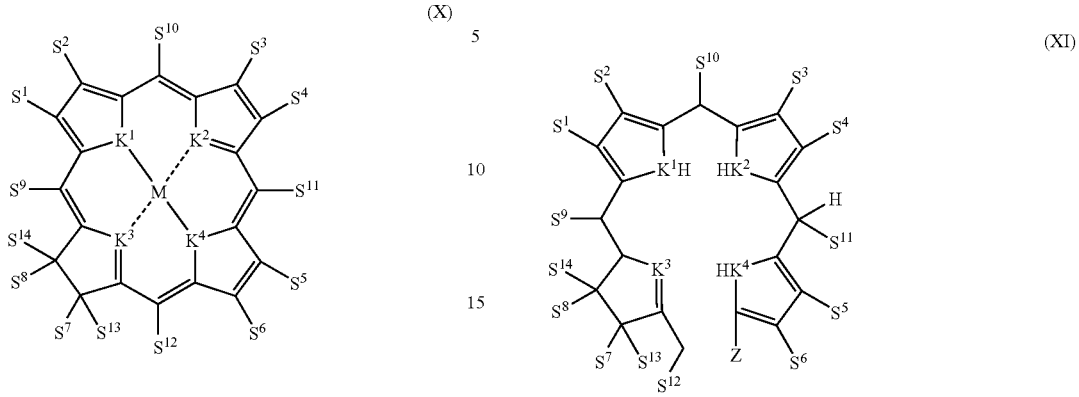

wherein:

M is a metal, such as a metal selected from the group consisting of Cu, Zn, Mg, Pt, Pd, Sn and Al, or M is absent;

$K^1$, $K^2$ and $K^4$ are atoms, such as atoms or hetero atoms independently selected from the group consisting of N, O, S, Se, Te, and CH (CH is less preferred and N is most preferred);

$K^3$ is N;

$S^1$, $S^2$, $S^3$, $S^4$ $S^5$, $S^6$, $S^7$, $S^8$, $S^9$, $S^{10}$, $S^{11}$, $S^{12}$, $S^{13}$, and $S^{14}$ are independently selected substituents, such as substituents selected from the group consisting of H, aryl, phenyl, cycloalkyl, alkyl, alkenyl, alkynyl, halogen, alkoxy, alkylthio, perfluoroalkyl, perfluoroaryl, pyridyl, cyano, thiocyanato, nitro, amino, alkylamino, acyl, sulfoxyl, sulfonyl, imido, amido, and carbamoyl.

In addition, from one to four of $S^1$, $S^2$, $S^3$, $S^4$ $S^5$, $S^6$, $S^7$, $S^8$, $S^9$, $S^{10}$, $S^{11}$, $S^{12}$, $S^{13}$, and $S^{14}$ may optionally be independently selected linking groups Q, for example linking groups Q of the formula:

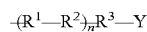

wherein:

n is from 0 or 1 to 5 or 10;

$R^3$ may be present or absent;

$R^1$, $R^2$, and $R^3$ are each independently selected from the group consisting of ethene, ethyne, aryl, and heteroaryl groups, which aryl and heteroaryl groups may be unsubstituted or substituted one or more times with H, aryl, phenyl, cycloalkyl, alkyl, alkenyl, alkynyl, halogen, alkoxy, alkylthio, perfluoroalkyl, perfluoroaryl, pyridyl, cyano, thiocyanato, nitro, amino, alkylamino, acyl, sulfoxyl, sulfonyl, imido, amido, and carbamoyl; and Y is a protected or unprotected reactive substituent, for example a reactive substituent selected from the group consisting of hydroxy, thio, seleno, telluro, ester, carboxylic acid, boronic acid, phenol, silane, sulfonic acid, phosphonic acid, alkylthiol, formyl, halo, alkenyl, alkynyl, haloalkyl, alkyl phosphonate, alkyl sulfonate, alkyl carboxylate, and alkyl boronate groups.

The method comprises oxidatively cyclizing a tetrahydrobilene of Formula XI:

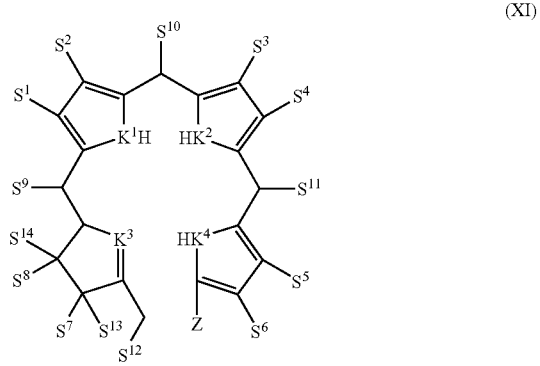

wherein Z is selected from the group consisting of halo, alkoxy, and acyloxy (preferably Br) (preferably in an organic solvent in the presence of a base, an oxidant and a metal salt $MX_n$, where X is an anion, and n is 2-3, to produce a compound of Formula X above), and then optionally displacing metal M to create a free base chlorin. Any suitable solvent may be employed, including polar or nonpolar solvents and protic or aprotic solvents. Suitable bases that may be used in the reaction include but are not limited to piperidine and 2,2,6,6-tetramethylpiperidine. Any suitable oxidant may be used, including simply air, oxygen, silver iodate, etc. In a preferred embodiment the cyclizing step is carried out in the presence of a silver salt such as silver triflate. The optional step of displacing metal M may be carried out with an acid in accordance with known techniques.

Structurally in compounds described herein, $S^1$ and $S^5$ may be independently selected trans-substituted linking groups Q, or $S^2$ and $S^6$ may be independently selected trans-substituted linking groups $Q^1$ and $Q^2$.

A second aspect of the present invention is a method of making a tetrahydrobilene of Formula XI:

(XI)

wherein $K^1$, $K^2$ $K^3$ and $K^4$ are as described above, and $S^1$, $S^2$, $S^3$, $S^4$ $S^5$, $S^6$, $S^7$, $S^8$, $S^9$, $S^{10}$, $S^{11}$, $S^{12}$, $S^{13}$, and $S^{14}$ are as described above; and Z is as described above. The method comprises condensing a compound of Formula WH with a compound of Formula EH

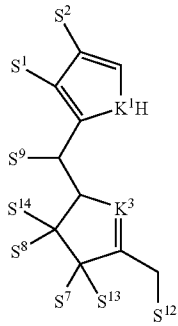
WH

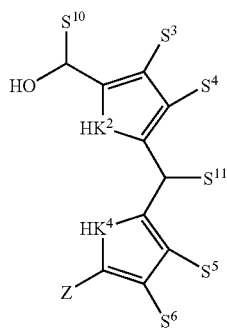
EH (preferably in an organic solvent in the presence of an acid) to form a tetrahydrobilene of Formula XI. Any suitable acid may be employed, such as a Bronsted or Lewis acid, one particular example being trifluoroacetic acid. The condensing step is preferably carried out under nonaqueous conditions. The organic solvent is preferably a polar or nonpolar aprotic solvent, such as acetonitrile, tetrahydrofuran or a mixture thereof.

The present invention further provides methods of making compounds of Formula WH, and the compounds so produced:

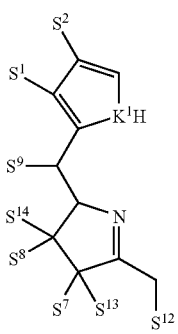
WH wherein $K^1$ is as given above, and $S^1$, $S^2$, $S^7$, $S^8$, $S^9$, $S^{12}$, $S^{13}$, and $S^{14}$ are as given above. The method comprises reacting a compound of Formula III

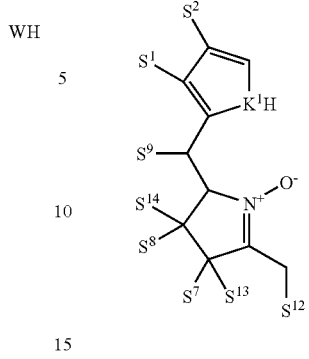
III in an organic solvent (preferably in the presence of Ti(0)) to form the compound of Formula WH.

A preferred group of compounds of Formula WH are those in which $S^1$ and $S^2$ are not simultaneously alkyl. One particularly preferred embodiment is compounds in which $S^1$ and $S^2$ are not simultaneously either alkyl or H (i.e., $S^1$ is not H or alkyl, and $S^2$ is not H or alkyl). In another particularly preferred embodiment, $S^1$ and/or $S^2$ are independently selected from the group consisting of Q, aryl, phenyl, cycloalkyl, alkenyl, alkynyl, halogen, alkoxy, alkylthio, perfluoroalkyl, perfluoroaryl, pyridyl, cyano, thiocyanato, nitro, amino, alkylamino, acyl, sulfoxyl, sulfonyl, imido, amido, and carbamoyl. In another particular preferred embodiment, $S^1$ and/or $S^2$ is a linking group Q as described above.

A further aspect of the present invention is a method of making a compound of Formula III:

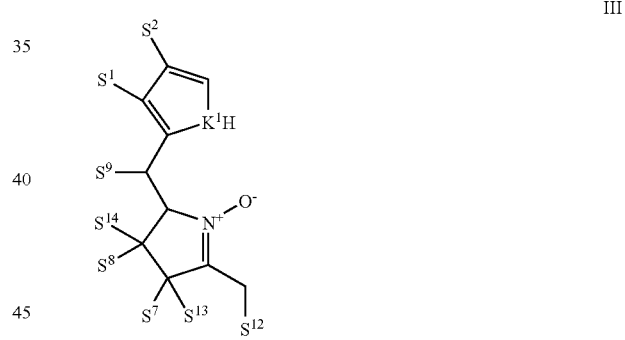
III wherein: $K^1$ is as given above, and $S^1$, $S^2$, $S^7$, $S^8$, $S^9$, $S^{12}$, $S^{13}$, and $S^{14}$ are as given above, and the compounds so produced. The method comprises cyclizing a compound of Formula II:

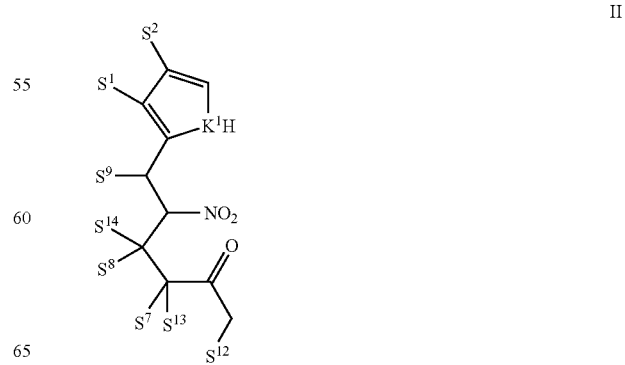
II (preferably in an organic solvent and preferably under reducing conditions, such as in the presence of zinc and acetic acid) to produce a compound of Formula III.

Synthesis of Oxochlorins. Oxochlorins may be considered as a particular type of chlorin. Oxochlorins and chlorins have similar spectral properties but the oxochlorins are more resistant to oxidation than are chlorins. In fact, oxochlorins have oxidation potentials similar to those of porphyrins whereas chlorins have lower oxidation potentials than porphyrins. Thus, broadly speaking, an oxochlorin has the spectral properties of a chlorin and the oxidation properties of a porphyrin.

The time-honored method for forming oxochlorins employs treatment of a β-substituted porphyrin with $OsO_4$ forming the vicinal diol, which upon acid-catalyzed pinacol rearrangement yields the oxochlorin bearing a geminal dialkyl group (Chang, C. K.; Sotiriou, C. *J. Heterocyclic Chem.* 1985, 22:1739-1741). However, application of this approach to porphyrin building blocks bearing specific patterns of substituents at the perimeter of the macrocycle typically results in a mixture of oxochlorins (Osuka, A., et al., *J. Am. Chem. Soc.* 1996, 118:155-168). Battersby found that the attempted synthesis of a chlorin by reaction of an Eastern half and a Western half in the presence of copper acetate in air afforded the oxochlorin directly (Battersby, A. R, et al., *J. Chem. Soc. Perkin Trans.* 1 1984, 2725-2732). He stated in his paper that spectral monitoring indicated the chlorin was forming first and then undergoing oxidation to give the oxochlorin. The same reaction in the absence of air afforded the chlorin. While the oxochlorin was an undesired byproduct in Battersby's synthesis, the oxochlorin incorporated the keto functionality at a specific site and did not occur as a mixture of isomers.

In our synthesis, we employ zinc acetate in air to, form the chlorin upon reaction of an Eastern half and a Western half. The chlorin so obtained can be oxidized to the oxochlorin, introducing the keto functionality adjacent to the geminal dimethyl group by oxidation of the isolated methylene group. Oxidation can be achieved by a variety of methods, including treatment with copper acetate and air, or oxidation with a number of reagents known to oxidize isolated methylene units. Such reagents include $SeO_2$, $MnO_2$, and $CrO_3$.

Statement of Utility. Chlorins (this term including oxochlorins) as described herein are useful for a variety of purposes known to those skilled in the art, including but not limited to the production of light harvesting arrays and solar cells as described in commonly owned, copending U.S. patent applications Ser. No. 09/621,797 and Ser. No. 09/621,091, both filed Jul. 21, 2000, the disclosures of both of which are incorporated by reference herein in their entirety.

The following examples are provided to illustrate certain aspects of the invention, and are not to be construed as limiting thereof.

EXAMPLE 1

Refined Syntheses of Meso-Substituted Chlorins via Tetrahydrobilene Intermediates In this Example, we describe a number of refinements that greatly facilitate access to chlorin building blocks. The synthesis of a new Western half (4) built around the tetrahydrodipyrrin nucleus is achieved by the deoxygenation of the corresponding N-oxide (3) under non-acidic conditions. The resulting tetrahydrobilene-α is stable, which enabled refinements to the conditions for both the condensation and the oxidation. We also have investigated a one-flask synthetic procedure for chlorin formation. Several new Eastern halves have also been prepared for enhanced solubility of the resulting chlorin building blocks in organic solvents. The meso-substituted chlorin building blocks are of interest in the synthesis of multi-chlorin arrays.

Synthesis of a Tetrahydrodipyrrin Western Half. The synthesis of the unsubstituted tetrahydrodipyrrin Western half 4 is shown in Scheme 2. The desired nitro-hexanone pyrrole 2 was prepared from pyrrole-2-carboxaldehyde by reaction with nitromethane, affording 2-(2-trans-nitrovinyl)pyrrole, followed by reduction with sodium borohydride and fluoride-mediated Michael addition of mesityl oxide. Reductive cyclization of 2 in the presence of Zn in acetic acid at room temperature as specified by Battersby ((1984) *J. Chem. Soc. Perkin Trans.* 1 (12):2725-2732) afforded the N-oxide 3 in <40% yield. A byproduct, observable by TLC analysis and estimated by $^1H$ NMR spectroscopy to be present in ~3:2 ratio (3:byproduct), was isolated and assigned the structure shown for 5 (Scheme 2). Noteworthy features of the $^1H$ NMR spectrum of 5 include the following: (1) the presence of two resonances due to the pyrrole β-protons, in contrast to the three resonances due to the α- and β-protons exhibited by the N-oxide 3, and (2) disappearance of the singlets assigned to the amino and pyrrolic NH protons upon exchange with $D_2O$. The formation of such a cyclic byproduct cannot occur with pyrrole precursors bearing a full complement of alkyl substituents at the α- and β-positions (Battersby, et al. (1984) *J. Chem. Soc. Perkin Trans.* 1 (12):2725-2732). The same reaction performed in acetic acid diluted 1:1 with ethanol (to lessen the exotherm) and held at 0° C., with portion-wise addition of the Zn, resulted in a >9:1 ratio of 3:5. The residual byproduct 5 was readily removed by chromatography. Under these improved conditions the desired N-oxide 3 was isolated in 86% yield.

The next step involved deoxygenation of N-oxide 3 to give the tetrahydrodipyrrin 4. Numerous methods have been developed for the deoxygenation of heterocyclic N-oxides bearing various functional groups (Katritzky and Lagowski, *Chemistry of the Heterocyclic N-Oxides*, Academic Press: London and New York, 1971, pp. 166-231; Ochiai, E. *Aromatic Amine Oxides*, Elsevier: Amsterdam, 1967, pp. 184-209; Albini, A.; Pietra, S. *Heterocyclic N-Oxides*, CRC Press: Boca Raton, 1991, pp. 120-134). For the tetrahydrodipyrrin N-oxide, the ideal deoxygenation method must not be strongly acidic to avoid polymerizing the pyrrole unit, and must not cause reduction of the imine. The deoxygenation of 3 was examined with a variety of reagents (Zn, NaOH/methanol (den Hertog, et al. (1952) *Rec. Trav. Chim. Pays-Bas.* 71:1145-1151); Zn, aqueous $NH_4Cl$/THF (Jiu and Mueller (1959) *J. Org. Chem.* 24:813-818; Aoyagi, et al. (August 1997) *Synthesis-Stuttgart* 891-894); $FeSO_4$, aqueous $NH_4Cl$/$CH_3CN$ (Talik and Plazek (1961) *Roczniki Chem.* 35:463-473); Mg, $AcONH_4$/methanol (Hahn and Lesiak (1985) *Polish J. Chem.* 59:627-629); Fe, $AcONH_4$/methanol (Hahn and Lesiak (1985) *Polish J. Chem.* 59:627-629); $Ph_3P$/toluene (Lu, et al. (1982) *Synthesis-Stuttgart* 185-186; Read, et al. (1983) *Aust. J. Chem.* 36:1227-1237); S/toluene (Relyea, et al. (1962) *J. Org. Chem.* 27:477-481); $NaN_3$/toluene (Di Nunno and Florio (1975) *La Chim. E L'Ind. (Milan)* 57:243-244); Zn, NaI, $Me_3SiCl$/$CH_3CN$ (Morita, et al. (1981) *Chem. Lett.* 921-924); at room temperature and at elevated temperatures but the N-oxide was resistant to deoxygenation with each of these reagents as determined by TLC or $^1H$ NMR analysis. In addition, $NaBH_4$/THF (Kawazoe and Tachibana (1965) *Chem. Pharm. Bull.* 13(9):1103-1107; Kawazoe and Araki (1968) *Chem. Pharm. Bull.* 16(5):839-847) reduced the N-oxide and the double bond affording several products. Treatment with $TiCl_3$ in a buffered $NH_4OAc$ solution (Battersby, et al. (1984) *J. Chem. Soc. Perkin Trans.* 1 (12):2725-2732) gave the pyrrolo-atropine byproduct 5 (obtained previously but not identified (Strachan, et al. (2000) *J. Org. Chem.* 65:3160-3172). This failure is in contrast to the successful transformation (75% yield) achieved by Battersby and coworkers upon applying the same method to a tetrahydrodipyrrin N[10]-oxide which differed from 3 only in bearing one ester and two alkyl substituents on the pyrrole unit (Battersby, et al. (1984) *J. Chem. Soc. Perkin Trans.* 1 (12):2725-2732). Similar pyrrolo[3.2.1]azabicyclooctane products have been reported by rearrangement of tetrahydrodipyrrin derivatives (formed as intermediates in amine+keto-aldehyde condensations in studies of aging) and a plausible mechanism proposed involving electrophilic attack of the pyrroline imine at the pyrrole 3-position (Xu and Sayre (1999) *Chem. Res. Toxicol.* 12:862-868).

Application of a procedure for the deoxygenation of N-oxides with Ti(0)/THF at room temperature (Malinowski, M. (1987) *Synthesis-Stuttgart* (8):732-734) to 3 resulted in a variety of decomposition products as determined by $^1$H NMR spectroscopy. Upon repeating the deoxygenation procedure with the addition of 2 molar equivalents of triethylamine to the Ti(0)/THF slurry (to neutralize the HCl liberated from the preparation of Ti(0)) prior to addition to the solution of 3 in THF, the desired deoxygenated product 4 was obtained as a crystalline solid following column chromatography. The tetrahydrodipyrrin 4 is quite stable, exhibiting negligible decomposition over one month upon storage at 0° C.

Scheme 2

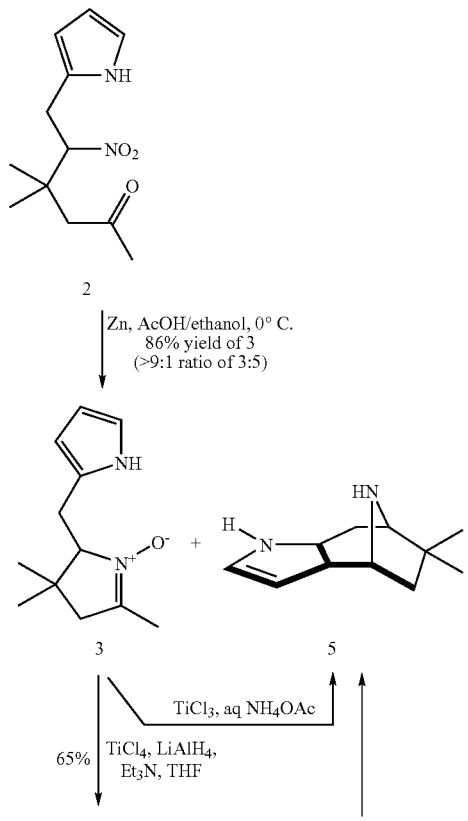

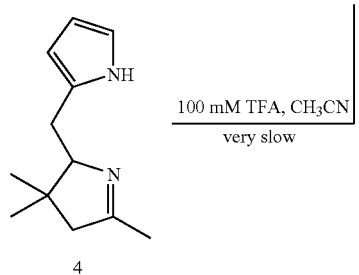

Investigation of the Synthesis of Chlorins. Our prior synthesis of chlorins involved (1) formation of the bromodipyrromethane-monocarbinol (Eastern half) by NaBH$_4$-reduction of the carbonyl group in the Eastern half precursor, (2) acid-catalyzed condensation of the Eastern half and the Western half to obtain the dihydrobilene-α, and (3) oxidative metal-mediated cyclization to give the chlorin (Strachan, et al. (2000) *J. Org. Chem.* 65:3160-3172; Balasubramanian, et al. (2000) *J. Org. Chem.* 65:7919-7929). All three steps were done in succession on the same day. However, condensation of 4 and 6a-OH (100 mM TFA in CH$_3$CN at room temperature) followed by oxidation under the conditions employed with 1 (excess AgIO$_3$, Zn(OAc)$_2$ and piperidine in anhydrous toluene at 80° C.) gave chlorin Zn-8a in only 7% yield. Similarly, reaction of 4 and 6c-OH afforded chlorin Zn-8c in 10% yield.

Studies of the Condensation. To understand whether the low yields of chlorin originated in the condensation process or the metal-mediated oxidative cyclization process, we sought to isolate the putative tetrahydrobilene-α, a linear tetrapyrrole derivative formed by condensation of the Western half and the Eastern half. The condensation of 4 and Eastern half 6a-OH (100 mM each) was performed at room temperature in CH$_3$CN containing 100 mM TFA (Eq 1). TLC analysis of the reaction mixture after 3 min. showed the presence of a new component. Chromatographic workup afforded the tetrahydrobilene-α 7a in 72% yield. The $^1$H NMR spectrum of the tetrahydrobilene-α showed resonances characteristic of the respective Western half 4 and Eastern half precursor 6a. The three signals (7.75, 8.05, 9.29 ppm) assigned to the pyrrolic NH units each appeared as a broad multiplet. The appearance of multiple signals is not unexpected: the tetrahydrobilene-α contains three chiral centers and the isolated product can comprise up to eight diastereomers. Bilanes and derivatives are known to be sensitive to oxidation as well as attack by electrophilic species (e.g., acids), and to undergo intermolecular exchange of the pyrrole rings (Xue and Scott (September 1998) *Tetrahedron Lett.* 39(37):6651-6654). However, the tetrahydrobilene-α sample showed no decomposition upon storage as a solid for several months or in a solution of CDCl$_3$ for more than two weeks under argon in the refrigerator.

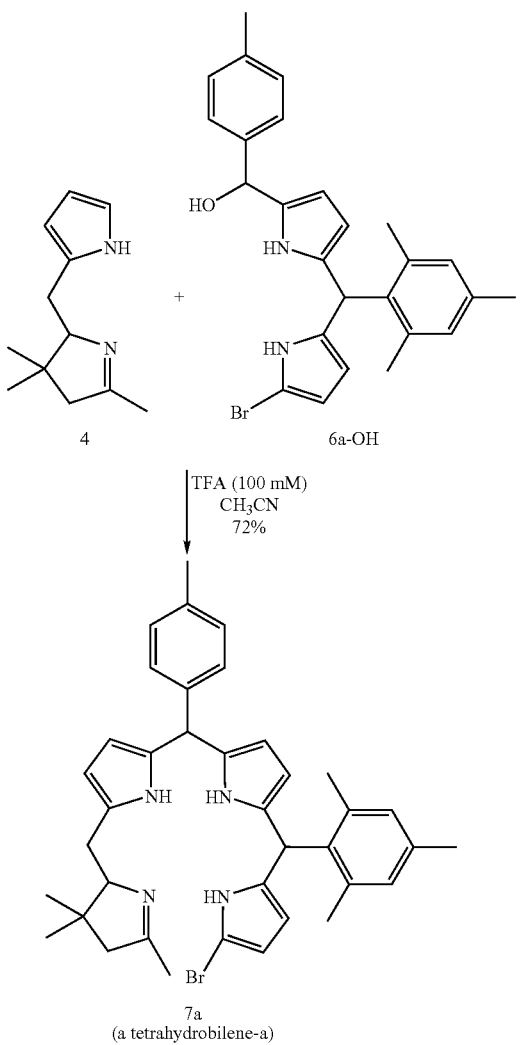

(1)

4    6a-OH

TFA (100 mM)
CH₃CN
72%

7a
(a tetrahydrobilene-a)

The surprising stability of the tetrahydrobilene-α and access to ~500 mg quantities of this material enabled us to explore the reaction conditions of the separate condensation and oxidation steps. To modify the conditions of the condensation, the concentration of TFA and the reaction time were examined. The condensation of Western half 4 and Eastern half 6a-OH was performed for a given period of time; for quantitation, the resulting tetrahydrobilene-α 7a was subjected to the oxidative cyclization to form the chlorin. The yield of the chlorin Zn-8a was then determined by UV-vis spectroscopy. Refined conditions for the oxidative cyclization were employed (vide infra); these conditions employ AgTf, Zn(OAc)₂ and 2,2,6,6-tetramethylpiperidine in CH₃CN at reflux in air for 4.5 h.

The effect of the concentration of TFA (10 mM to 316 MM) was examined at room temperature for condensations of 30 min in CH₃CN. The results are shown in FIG. 1. The chlorin was formed in 51% yield upon use of 100 mM TFA. By contrast, the reaction of the dihydrodipyrrin (1) was performed with 10 mM reactants and 10 mM TFA, and yields of chlorin were ~10-20%.

Two possible side reactions during acid catalyzed condensation were of considerable concern, including rearrangement of the Western half and acidolytic scrambling: (1) A likely mechanism for formation of byproduct 5 involves electrophilic attack of the positively charged imine (or nitrone) on the 3-position of the pyrrole. Treatment of 4 (100 mM) under the same acid catalysis conditions (100 mM TFA in CH₃CN at room temperature) gave a ratio of 95:5 for compounds 4:5 after 30 min but ~20:80 after 12 h. The same reaction with 1 M TFA gave ~15:85 after 30 min. These results show that the rearrangement of the Western half 4 to the byproduct 5 occurs under acid catalysis but the reaction is too slow to be competitive with the condensation with an Eastern half giving the tetrahydrobilene-α. (2) A key concern upon exposure of dipyrromethanes to acidic media is the occurrence of acidolysis yielding fragments that can recombine to form products with undesired substitution patterns (i.e., scrambling) (Littler, et al. (1999) *J. Org. Chem.* 64:2864-2872). We have found that dipyrromethane-carbinols (and the resulting porphyrinogens) are stable to modest concentrations of TFA in CH₃CN but that scrambling occurs within 30 min upon exposure to 100 mM TFA (Rao, et al. (2000) *J. Org. Chem.* 65:7323-7344; Rao et al. (2000) *J. Org. Chem.* 65:1084-1092). LD-MS analysis of the crude reaction mixture showed no scrambling with condensations employing 100 mM TFA. The absence of scrambling in the condensation of the Eastern and Western halves at higher acid concentration than in dipyrromethane condensations can be explained by consideration of the basicity of the different reactants. The weakly basic nature of the pyrrolic unit in a dipyrromethane (protonated 2-methylpyrrole has $pK_a$=-0.21) (Chiang and Whipple (1963) *J. Am. Chem. Soc.* 85:2763-2767) provides little capacity for buffering of the acid in reactions of the dipyrromethane. By comparison, the pyrroline motif in the Western half is basic (protonated 2,4,4-trimethyl-$\Delta^1$-pyrroline has $pK_a$=7.6) (Bonnett, et al. (1959) *J. Chem. Soc.* 2087-2093). With equal concentrations of TFA and the Western half (100 mM each) the latter likely buffers the former, affording an effective acidity within the range that safely avoids acidolysis of the dipyrromethane or tetrahydrobilene-α species.

Figure 2:
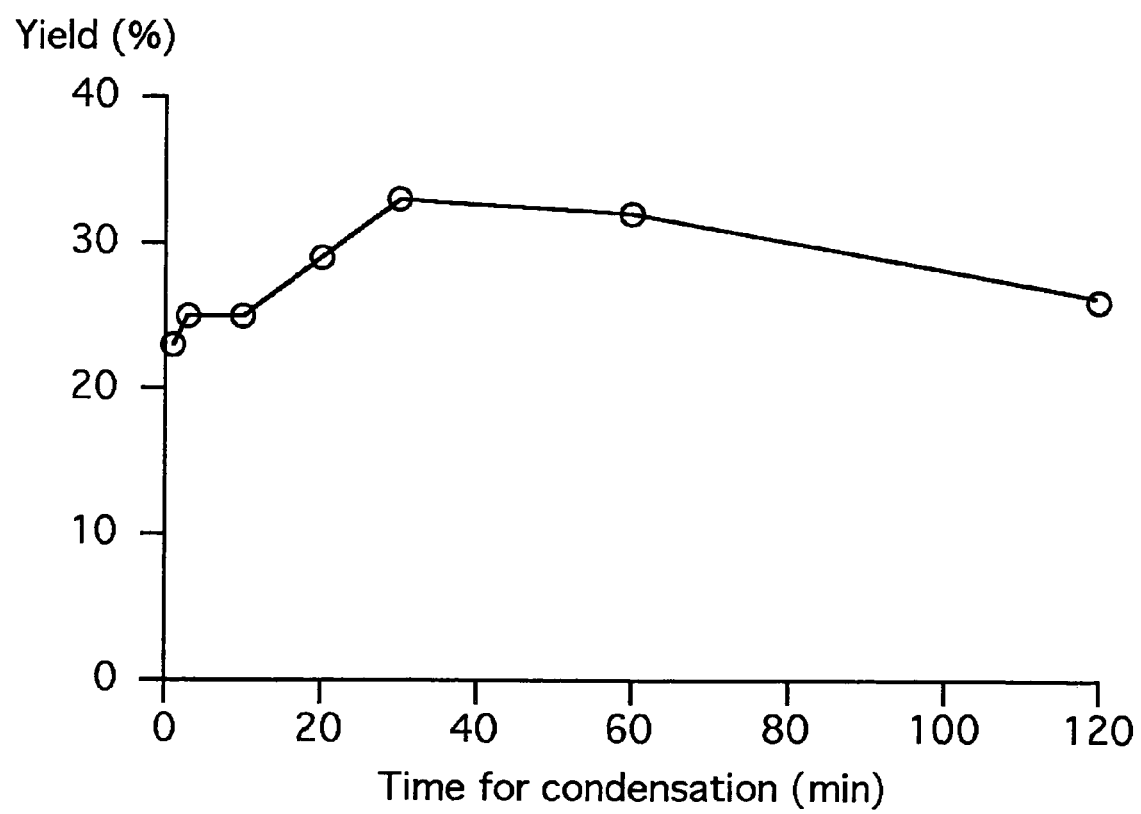
FIG. 2 shows the effect of the duration of the condensation of Eastern half (6a-OH) and Western half (4) on the ultimate yield of chlorin. The yield shown refers to the amount of chlorin formed upon treatment of the crude product to the oxidation conditions (analogous to a one-flask reaction) followed by UV-Vis spectroscopy.

The time course of the condensation for reactions with 100 mM TFA at room temperature is shown in FIG. 2. These results show that the reaction is rapid and the yield changes only slightly over the course of 2 h, with a slight peak around 30 min. In summary, a condensation for 30 min at room temperature in CH₃CN containing 100 mM TFA results in the highest yield of chlorin.

Studies of the Metal-Mediated Oxidative Cyclization. While very little is known either about the intermediates or the sequence of events in this process, consideration of the formal transformations in the overall process guided our thinking in the development of reaction conditions. The role of the oxidant is to remove 6 electrons and 6 protons. The role of the base is to neutralize the acetic acid (2 equiv) formed upon zinc insertion and the HBr formed upon aromatization, and perhaps to facilitate imine-enamine tautomerization. The role of the metal complex is to template the electrocyclization. The role of the silver salt is to facilitate dehydrobromination. The overall process is expected to be complex. For example, oxidation is likely to occur in multiple steps, interspersed in which may be complexation and other processes.

The conversion of the tetrahydrobilene-α 7a to the zinc chlorin Zn-8a was examined under a variety of conditions. The conditions employed previously used AgIO₃ (15 mol equiv) Zn(OAc)₂ (15 mol equiv) and piperidine (15 mol equiv) in toluene at 80° C. for 2 h. The same conditions with 7a gave the desired zinc chlorin Zn-8a; the yield was low (7%) but a more severe problem was that iodinated chlorin byproducts were occasionally obtained. To avoid use of AgIO₃, we reexamined the use of high-potential quinones such as p-chloranil and DDQ, which are effective oxidants in the two-step one-flask synthesis of porphyrins (Lindsey, J. S. In *The Porphyrin Handbook*; Kadish, K. M.; Smith, K. M.; Guilard, R., Eds.; Academic Press: San Diego, Calif. 2000, Vol. 1, pp 45-118). We previously attempted to use p-chloranil but the chlorin product formed gave an incorrect molecule ion peak upon LD-MS analysis. The use of p-chloranil with the tetrahydrobilene-α gave two covalent chlorin-hydroquinone byproducts in greater yields than that of the desired chlorin. Quinones of lower potential such as duroquinone in the presence of additives (e.g., AgTf, AgBF$_4$) resulted in facile formation of the desired chlorin in yields of 60-70%, but we subsequently found that omission of the duroquinone caused no change in the yield. From this result, the oxidation was ascribed to O$_2$ in air. (It is likely that the oxidant in the previous reaction conditions employing AgIO$_3$ also was O$_2$.) This observation ultimately led to the following reaction conditions: AgTf (3 mol equiv), Zn(OAc)$_2$ (15 mol equiv) and 2,2,6,6-tetramethylpiperidine (15 mol equiv) in a solvent exposed to air. The following sections describe the iterative optimization process that led to these reaction conditions. The cleanliness of these reactions enabled the yield of chlorin to be determined by UV-vis spectroscopy.

We first examined the conversion of 7a into Zn-8a in ten solvents of diverse polarity and composition (Table 1). Acetonitrile, THF, and DMF were the best solvents (~60% yield) but we focused on acetonitrile and THF for further studies because of their ease of handling. It is noteworthy that reagent-grade THF gave a slightly higher yield of chlorin (Zn-8a) compared to that with distilled THF.

TABLE 1[a]

| Solvent | Temp. (° C.) | Yield (%)[b] |
| --- | --- | --- |
| CH$_3$CN | reflux | 60 |
| THF | reflux | 58 |
| DMF | 120° C. | 57 |
| 1,2-dichloroethane | reflux | 44 |
| DMSO | 120° C. | 42 |
| Toluene | reflux | 39 |
| Ethanol | reflux | 35 |
| pyridine | reflux | 34[c] |
| CHCl$_3$ | reflux | 19 |
| dioxane | reflux | 17 |
| methanol | reflux | <1[c] |

[a]All reactions were performed under the standard conditions employing the following components: tetrahydrobilene-a (7a) (10 mM), AgTf (3 mol equiv), Zn(OAc)$_2$ (15 mol equiv), 2,2,6,6-tetramethylpiperidine (15 mol equiv) under the specified conditions (solvent, temperature) exposed to air for 4.5 h.
[b]Determined by absorption spectroscopy ($\epsilon_{609}$ = 43,600 M$^{-1}$cm$^{-1}$) in toluene.
[c]The long wavelength $\lambda_{max}$ was at 612 nm.

Four amine bases were examined (Table 2) in THF or acetonitrile. Of the 4 amines examined, 2,2,6,6-tetramethylpiperidine gave the best results in both acetonitrile and THF (72%, 65%). Piperidine, which was used in the previous method, gave a low yield.

TABLE 2[a]

| | Yield (%)[b] | |
| Base | THF | CH$_3$CN |
| --- | --- | --- |
| 2,2,6,6-tetramethylpiperidine | 65 | 72 |
| triethylamine | 35 | 57 |
| piperidine | 41[c] | 31 |
| 2,5-di-tert-butylpyridine | <1 | <1 |

[a]All reactions were performed under the standard conditions employing the following components: tetrahydrobilene-a (7a) (10 mM), AgTf (3 mol equiv), Zn(OAc)$_2$ (15 mol equiv), specified base (15 mol equiv) at reflux in the specified solvent exposed to air for 4.5 h.
[b]Determined by absorption spectroscopy ($\epsilon_{609}$ = 43,600 M$^{-1}$cm$^{-1}$) in toluene.
[c]The long wavelength $\lambda_{max}$ was at 612 nm.

We examined the amount of AgTf required for the reaction (Table 3). When a large excess of AgTf was used, little chlorin Zn-8a was formed. The best result was obtained using 2 to 5 mol equiv of AgTf.

TABLE 3[a]

| Mol equiv of AgTf | Yield (%)[b] |
| --- | --- |
| 1 | 46 |
| 2 | 60 |
| 3 | 63 |
| 5 | 68 |
| 10 | 7 |
| 15 | —[c] |

[a]All reactions were performed under the standard conditions employing the following components: tetrahydrobilene-a (7a) (10 mM), AgTf (specified amount), Zn(OAc)$_2$ (15 mol equiv), 2,2,6,6-tetramethylpiperidine (15 mol equiv) at reflux in CH$_3$CN exposed to air for 4.5 h.
[b]Determined by absorption spectroscopy ($\epsilon_{609}$ = 43,600 M$^{-1}$cm$^{-1}$) in toluene).
[c]The broad bands in the absorption spectrum precluded accurate yield determination.

To establish the absolute requirement for each of the reagents in the chlorin-forming reaction, omission experiments were performed (Table 4). In the absence of AgTf, chlorin was formed at only one-half to one-fourth of the normal level. No chlorin was observed in the absence of zinc acetate, and only a trace was obtained in the absence of 2,2,6,6-tetramethylpiperidine.

TABLE 4[a]

| | Yield (%)[b] | |
| Conditions | THF | CH$_3$CN |
| --- | --- | --- |
| No omission (standard conditions) | 58 | 60 |
| Omission of AgTf | 15 | 35 |
| Omission of Zn(OAc)$_2$ | — | 0 |
| Omission of 2,2,6,6-tetramethylpiperidine | — | <1 |

[a]All reactions were performed under the following conditions (with omission of the specified component): tetrahydrobilene-a (7a) (10 mM), AgTf (3 mol equiv), Zn(OAc)$_2$ (15 mol equiv), 2,2,6,6-tetramethylpiperidine (15 mol equiv) at reflux in the specified solvent exposed to air for 4.5 h.
[b]Determined by absorption spectroscopy ($\epsilon_{609}$ = 43,600 M$^{-1}$cm$^{-1}$) in toluene.

The concentration dependence of the reaction was examined by performing the reaction of the tetrahydrobilene-α 7a at 1, 3 or 10 mM and scaling the concentrations of the reagents linearly. The yield of chlorin was essentially constant over this 10-fold change in concentration.

Figure 3:
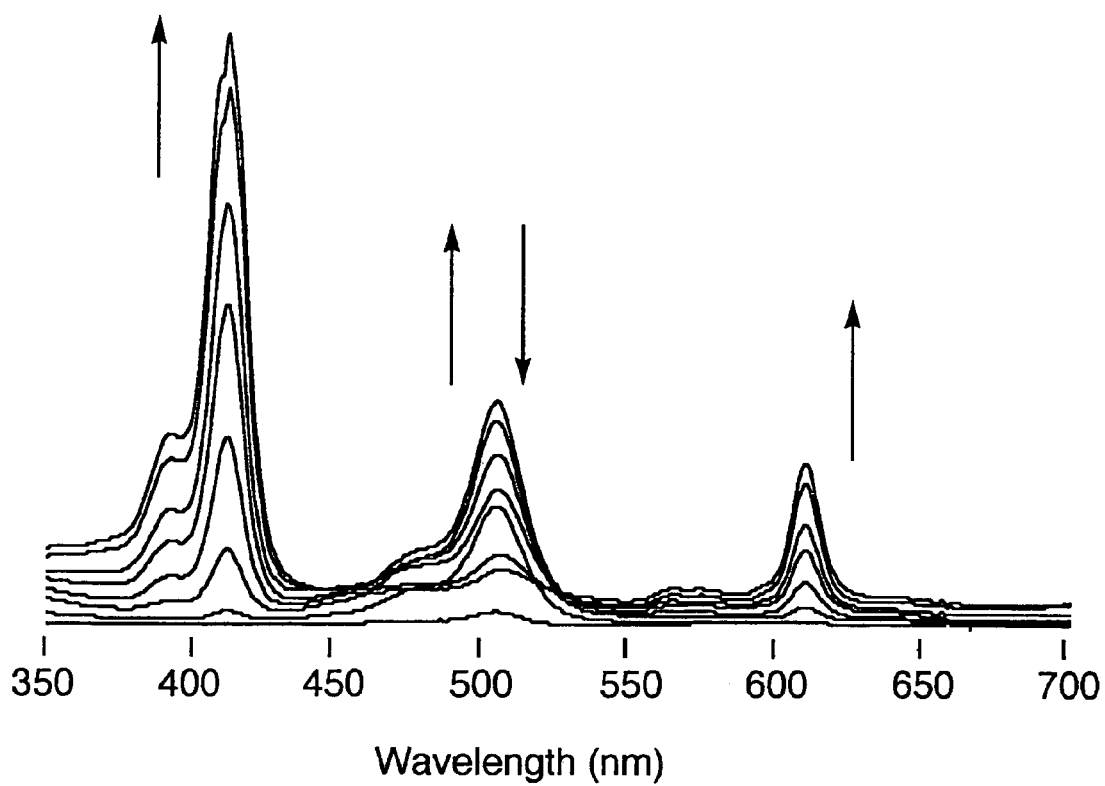
FIG. 3 shows the spectral evolution of the conversion of 7a to Zn-8a upon treatment to the oxidation conditions [tetrahydrobilene-α (7a) (10 mM), AgTf (3 mol equiv), $Zn(OAc)_2$ (15 mol equiv), 2,2,6,6-tetramethylpiperidine (15 mol equiv) in $CH_3CN$ at reflux in air]. Time points shown were taken at 1 min, 3 min, 8 min, 15 min, 35 min, 1 h, 2 h, and 5 h. The absorption peaks at the Soret band and at the $Q_y(0,0)$ band increase with time. The absorption peak at 505 nm rises and declines with time (from lowest to highest intensity the times were 1 min, 5 h, 2 h, 3 min, 1 h, 35 min, 8 min, and 15 min).
Figure 4:
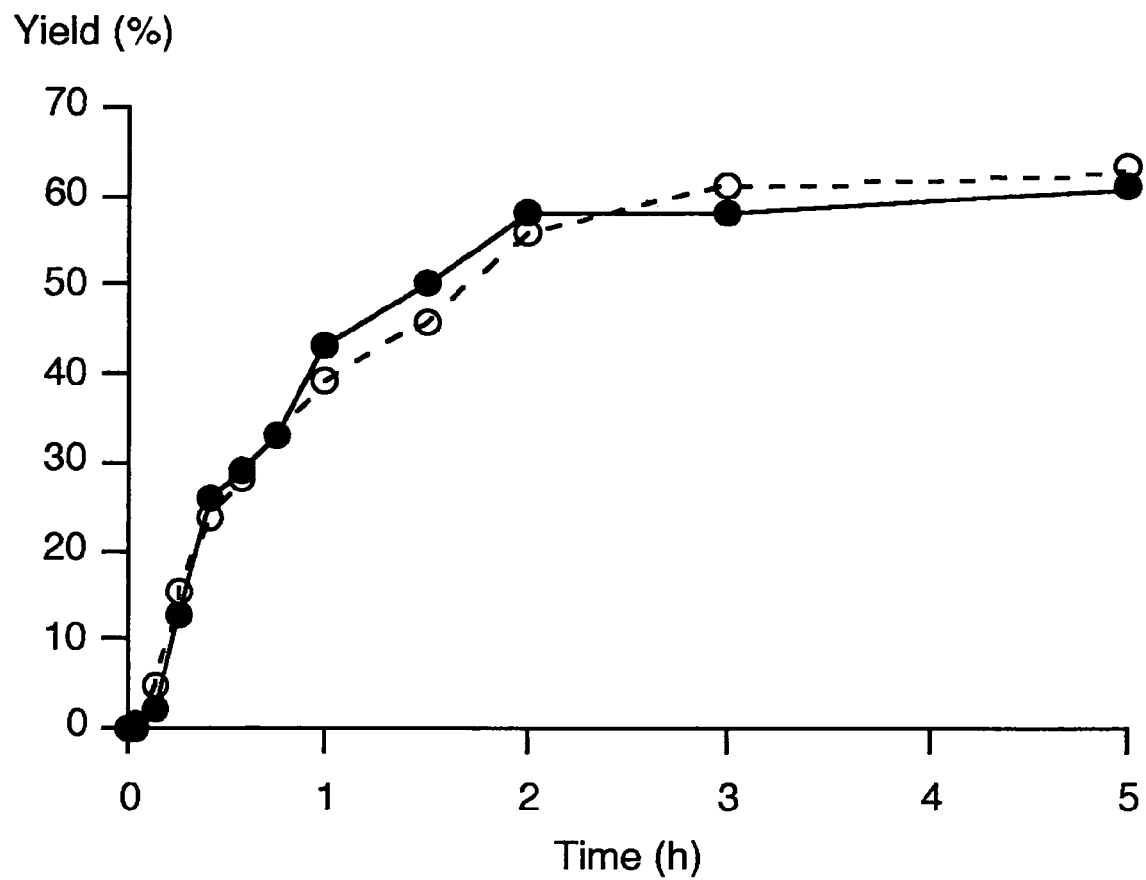
FIG. 4 shows the yield of chlorin Zn-8a as a function of time upon treatment of 7a to the oxidation conditions [tetrahydrobilene-α (7a) (10 mM), AgTf (3 mol equiv), $Zn(OAc)_2$ (15 mol equiv), 2,2,6,6-tetramethylpiperidine (15 mol equiv) in $CH_3CN$ at reflux in air]. The yield was determined by absorption spectroscopy ($\epsilon_{609}$=43,600 $M^{-1}cm^{-1}$) in toluene. Solid circles, THF; open circles, $CH_3CN$.

The time course of the reaction was monitored by absorption spectroscopy. The spectral evolution of the oxidation process is shown in FIG. 3. Within one minute, a sharp absorption band is evident at 505 nm, which resembles that of a zinc-bis(dipyrrinato) chromophore (Granick and Gilder, In *Advances in Enzymology*; Nord, F. F. Ed.; Interscience: New York, 1947; Vol. 7, pp 358-363; Johnson, et al. (1959) *J. Chem. Soc.* 3416-3424; Motekaitis and Martell (1970) *Inorg. Chem.* 9:1832-1839; March, et al. (1971) *J. Chem. Soc. (A)* 440-448; Murakami, et al. (1973) *J. Chem. Soc. Dalton Trans.* 1734-1737; Hill and Williamson (1985) *J. Chem. Soc., Chem. Commun.* 1228-1229; Brückner, et al. (1996) *Can. J. Chem.* 74:2182-2193) but such an assignment is not certain (see EXAMPLE 3). A zinc-dipyrrin could form by chelation of a partially oxidized product of the initial tetrahydrobilene-α. The peak at 505 nm increased as the reaction proceeded for 35 min and then decreased. The absorption spectra also show the appearance after 8 min of the characteristic chlorin peaks at 413 and 609 nm, which continue growing in over 1 h. After 1 h, more than 40% of tetrahydrobilene-α 7a had been converted into chlorin Zn-8a. The yield of chlorin as a function of time was readily assessed based on the intensity of the peak at 609 nm. The resulting yield versus time plot is shown in FIG. 4. The formation of the chlorin Zn-8a is essentially complete within 5 h.

In summary, the conditions for converting the tetrahydrobilene-α into the chlorin are as follows: tetrahydrobilene-α (10 mM), AgTf (3 to 5 mol equiv), Zn(OAc)$_2$ (15 mol equiv), and 2,2,6,6-tetramethylpiperidine (15 mol equiv) in acetonitrile at reflux in air for 4 to 6 h. These conditions were applied to a larger-scale synthesis of chlorin Zn-8a. Thus, 75.8 mg of tetrahydrobilene-α 7a was converted to 45 mg of chlorin Zn-8a in 62% yield.

One-Flask Procedure for Synthesis of Chlorins. The condensation yielding a tetrahydrobilene-α and subsequent oxidative cyclization yielding the chlorin has heretofore been implemented in a sequential two-flask procedure. The first step is an intermolecular reaction and should not require dilute conditions; the second step is an itramolecular cyclization and should proceed in greater yield under dilute conditions. Accordingly, we investigated a one-flask procedure employing 100 mM reactants in the condensation procedure and 10 mM reactants in the cyclization procedure. After condensation of Western Half (4) and Eastern half 6a-OH using 100 mM of TFA in acetonitrile, the reaction mixture was diluted 10-fold by addition of CH$_3$CN. The components for the oxidation were added [AgTf (3 mol equiv), Zn(OAc)$_2$ (15 mol equiv) and 2,2,6,6-tetramethylpiperidine (30 mol equiv rather than 15 equiv, to neutralize the TFA)] and the mixture was refluxed with exposure to air. After 18 h, the reaction mixture was chromatographed, affording chlorin Zn-8a in 31% yield (Eq 2). Although this one-flask approach is simple and readily implemented, the two-flask process affords a higher yield (45%) of chlorin.

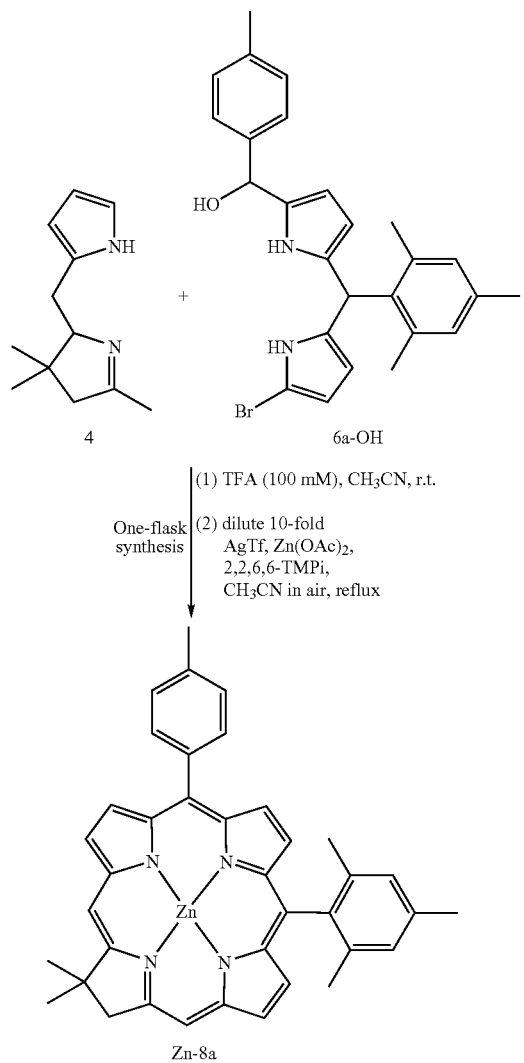

(2)

Extension to the Synthesis of Meso-Substituted Chlorins. We investigated the synthesis of meso-substituted chlorins bearing two types of substituents: (1) strong electron-withdrawing groups and (2) synthetic handles at defined locations at the perimeter of the macrocycle. The former establish the scope of the methodology and the latter enable construction of chlorin-containing model systems in biomimetic or materials chemistry.

The synthesis of meso-substituted Eastern halves follows established methodology for the one-flask synthesis of meso-substituted dipyrromethanes (Littler, et al. (1999) *J. Org. Chem.* 64(4):1391-1396), monoacylation of a dipyrromethane (Rao, et al. (2000) *J. Org. Chem.* 65(4):1084-1092), and monobromination of a dipyrromethane (Strachan, et al. (2000) *J. Org. Chem.* 65:3160-3172). The precursors to meso-substituted Eastern halves 6b-e have been prepared (Scheme 3). The dipyrromethanes 9b-e (Rao, et al. (2000) *J. Org. Chem.* 65(4):1084-1092) were treated with ethylmagnesium bromide followed by pyridyl thioesters (10-12)(Strachan, et al. (2000) *J. Org. Chem.* 65:3160-3172; Goto, et al. (1980) *Chem. Lett.* (1):51-52) affording monoacyldipyrromethanes 13b-e in 54-60% yield. Bromination of the latter by treatment with NBS in THF at −78° C. afforded the desired precursor to the Eastern halves 6b-e in 65-84% yield.

While all of the tetrahydrobilenes (7a-f) were stable for a period of ≧1 month, the Eastern half precursors (1-bromo-9-aroyldipyrromethanes) exhibited a range of stability. Compounds 6a-c or 6d showed decomposition after a few days or one week, respectively, while 6e and 6f were stable for >1 month.

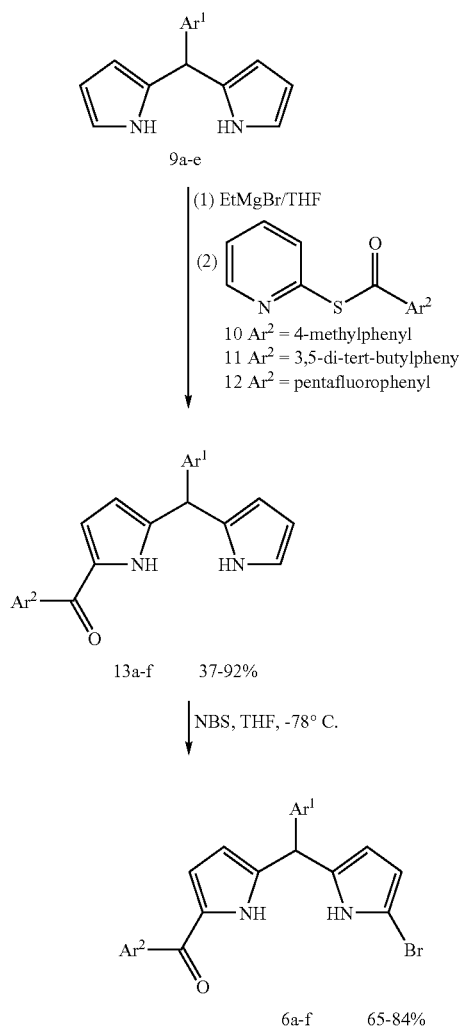

Scheme 3

9a-e (1) EtMgBr/THF
(2)

10 Ar² = 4-methylphenyl
11 Ar² = 3,5-di-tert-butylphenyl
12 Ar² = pentafluorophenyl 13a-f   37-92%

NBS, THF, -78° C.

6a-f   65-84% structures of Ar¹ and Ar² are shown in Chart 1

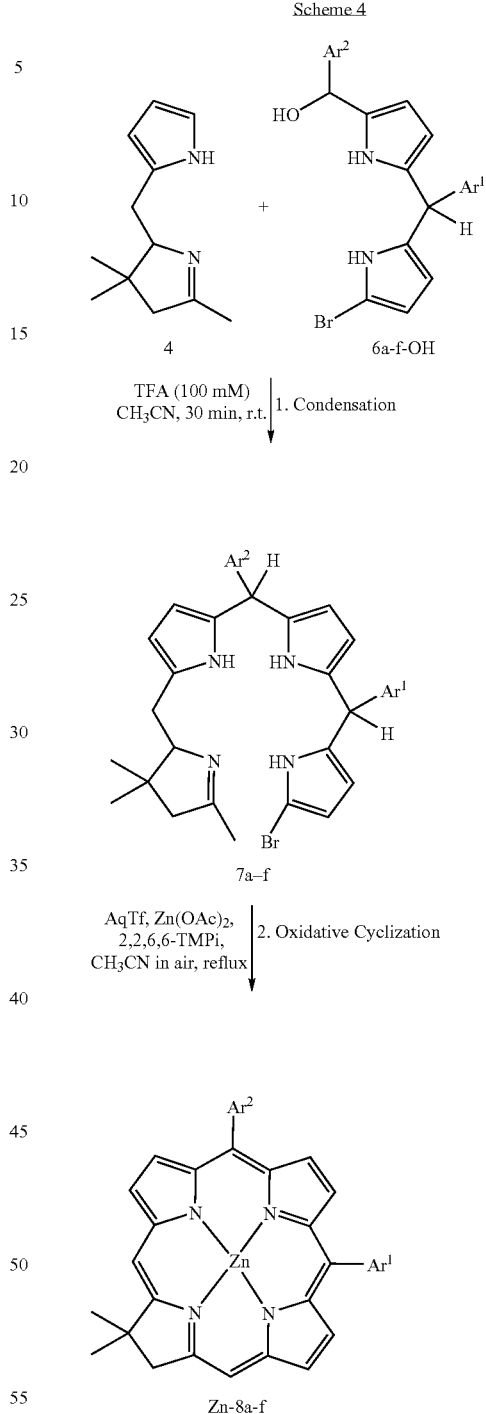

Scheme 4

4     6a-f-OH

TFA (100 mM)
CH₃CN, 30 min, r.t. | 1. Condensation 7a-f

AqTf, Zn(OAc)₂,
2,2,6,6-TMPi,
CH₃CN in air, reflux | 2. Oxidative Cyclization

Zn-8a-f

The synthesis of meso-substituted chlorin building blocks was carried out by the two-flask method as shown in Scheme 4. This route is to be compared with the previous route shown in Scheme 1. In each case, the new Western half 4 was employed. In these preparative syntheses, the oxidative cyclization process was monitored by absorption spectroscopy, showing the rise and fall of the intermediate ($\lambda_{abs}$ ~505 nm) and the formation of the chlorin ($\lambda_{abs}$ ~609 nm). In general the oxidative cyclization was nearly complete at 4-8 h but the reactions were often continued for up to 24 h.

The various meso-substituted chlorins prepared via this method are shown in Chart 1. The synthesis of chlorin Zn-8a provides a benchmark for yield comparisons. The reaction of 4 and 6a-OH afforded tetrahydrobilene 7a in 72% yield; oxidative conversion of the latter afforded Zn-8a in 62% yield. The reaction of the bis(pentafluorophenyl)-substituted Eastern half with 4 gave the tetrahydrobilene 7b in 32% yield and the chlorin Zn-8b in 38% yield. Several chlorin building blocks were prepared. The reaction of the Eastern half bearing a TMS-protected ester (6c-OH) with 4 gave the tetrahydrobilene 7c and chlorin Zn-8c in reasonable yields (55%, 41%). An iodo-substituted chlorin (Zn-8d) was prepared by reaction of the corresponding Eastern half 6d. We attempted to prepare a chlorin bearing a trimethylsilyl-protected ethyne by reaction of Eastern half 6e. The tetrahydrobilene 7e was formed smoothly. However, oxidative cyclization afforded the chlorin with the ethyne lacking the trimethylsilyl protecting group (Zn-7e). The synthesis of a similar trimethylsilyl-protected ethyne chlorin was attempted with oxidative cyclization of tetrahydrobilene 7f in THF rather than $CH_3CN$ and again the deprotected ethynyl chlorin (Zn-8f) was obtained. In two cases a comparison was made of the oxidative cyclization in $CH_3CN$ or in THF; in each case (7d, 7e) the yield of zinc chlorin was slightly higher in THF. Zinc chlorins Zn-7d and Zn-7e both incorporate the 3,5-di-tert-butyl group for increased solubility in organic solvents. In no case was scrambling yielding a mixture of chlorins detected.

It is noteworthy that in each synthesis the intermediate tetrahydrobilene-α was isolated in substantial quantities (73-460 mg), characterized, and found to be reasonably stable. The yields of chlorins were 2-4-fold greater than those obtained previously where comparisons could be made. For example, the prior synthetic method afforded chlorins Zn-8a, Zn-8b, or Zn-8c in yields of 10, 6, or 10% (see Experimental), respectively, to be compared with 45, 12, or 23% in the current method. Note that the deprotected ethynyl chlorin Zn-8f was obtained herein in 30% yield, in contrast to the 9% yield of the protected ethynyl chlorin by the previous method.

CHART 1

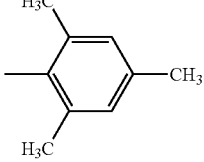

| | $Ar^1$ | $Ar^2$ | Stepwise Yields (%) | | Total Yield (%) |
| --- | --- | --- | --- | --- | --- |
| | | | Tetrahydrobilene 7 | Chlorin Zn-8 | |
| a | 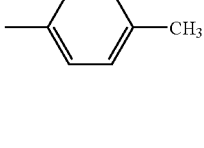 | 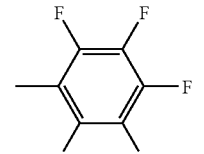 | 72 | 62 | 45 |
| b | 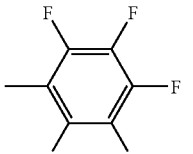 | 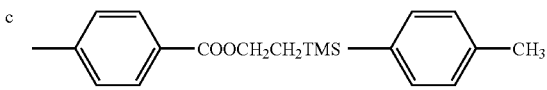 | 32 | 38 | 12 |
| c | 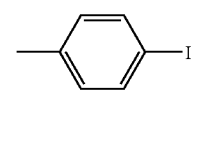 —COOCH₂CH₂TMS | —⟨⟩—CH₃ | 55 | 41 | 23 |
| d | 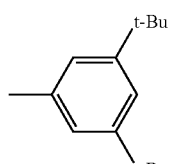 | | 40 | 40 (43) | 16 |

CHART 1-continued

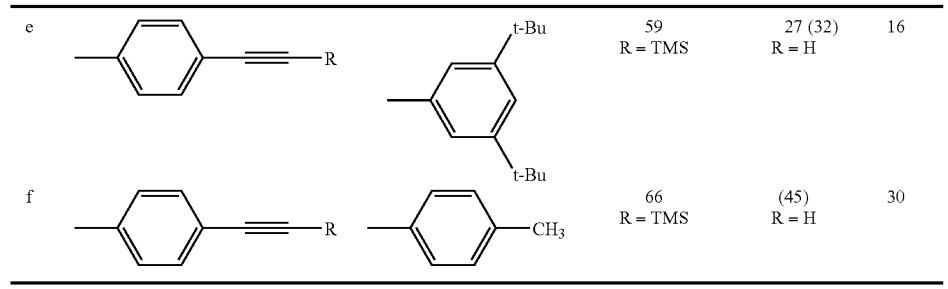

| | | | | |
|---|---|---|---|---|
| e | | 59 R = TMS | 27 (32) R = H | 16 |
| f | | 66 R = TMS | (45) R = H | 30 |

(yields in parentheses were obtained in THF rather than CH$_3$CN)

General Experimental Methods.

$^1$H and $^{13}$C NMR spectra (300 MHz) were collected in CDCl$_3$ unless noted otherwise. Absorption spectra were obtained in toluene at room temperature. Chlorins were analyzed by laser desorption mass spectrometry (LD-MS) in the absence of a matrix (Fenyo, et al. (1997) *J. Porphyrins Phthalocyanines* 1:93-99; Srinivasan, et al. (1999) *J. Porphyrins Phthalocyanines* 3:283-291). Fast atom bombardment mass spectrometry (FAB-MS) data are reported for the molecule ion or protonated molecule ion. Pyrrole was distilled at atmospheric pressure from CaH$_2$. Melting points are uncorrected. p-Iodobenzaldehyde was obtained from Karl Industries, Inc. All other reagents and starting materials were obtained from Aldrich. Column chromatography was performed with flash silica (Baker). The reduction yielding the Eastern half was performed following a standard procedure for forming dipyrromethane-carbinols (Rao et al. (2000) *J. Org. Chem.* 65:1084-1092).

Solvents. THF was distilled from sodium benzophenone ketyl as required. Toluene was distilled from CaH$_2$. CH$_3$CN (Fisher certified A.C.S.) for use in the condensation process was distilled from CaH$_2$ and stored over powdered molecular sieves. Nitromethane was stored over CaCl$_2$. Anhydrous methanol was prepared by drying over CaH$_2$ for 12 h followed by distillation. Other solvents were used as received.

Non-commercial compounds. The compounds 2, 6a, 6b, 6f, 10, 12, 13a, 13b and 13f were prepared as described in the literature (Strachan, et al. (2000) *J. Org. Chem.* 65:3160-3172). The compounds 9a-d (Littler, et al. (1999) *J. Org. Chem.* 64:1391-1396) and 9e (Cho, et al. (1999) *J. Org. Chem.* 64:7890-7901) also were prepared as described in the literature.

1,3,3-Trimethyl-2,3,4,5-tetrahydrodipyrrin N$^{10}$-oxide (3). Following a general procedure (Battersby, et al. (1984) *J. Chem. Soc. Perkin Trans.* 1 (12):2725-2732), to a vigorously stirred solution of 1-(2-pyrrolyl)-2-nitro-3,3-dimethyl-5-hexanone 2 (1.26 g, 5.29 mmol) in 25 mL of acetic acid and 25 mL of ethanol at 0° C., zinc dust (8.64 g, 132 mmol) was added slowly in small portions for 5 min. The reaction mixture was stirred at 0° C. for 15 min, and then was filtered through Celite. The filtrate was concentrated under high vacuum. The resulting brown solid was purified by column chromatography [silica; packed and eluted with ethyl acetate/ CH$_2$Cl$_2$ (1:1), then eluted with CH$_2$Cl$_2$/methanol (9:1)] affording a brown oil that solidified to brownish crystals on standing at room temperature (943 mg, 86%): mp 85-87° C.; $^1$H NMR δ 1.12 (s, 3H), 1.17 (s, 3H), 2.04 (s, 3H), 2.28 (d, J=17.6 Hz, 1H), 2.44 (d, J=17.6 Hz, 1H), 2.95-3.10 (m, 2H), 3.82-3.96 (m, 1H), 5.85-5.97 (m, 1H), 6.02-6.11 (m, 1H), 6.64-6.72 (m, 1H), 10.50-10.72 (br, 1H); $^{13}$C NMR δ 13.9, 23.4, 26.3, 28.5, 37.8, 47.7, 81.9, 107.0, 107.9, 118.1, 129.2, 147.3; FAB-MS obsd 206.1415, calcd 206.1419 (C$_{12}$H$_{18}$N$_2$O).

1,3,3-Trimethyl-2,3,4,5-tetrahydrodipyrrin (4). Following a general procedure for the deoxygenation of N-oxides (Malinowski, M. (August 1987) *Synthesis-Stuttgart* (8):732-734) with slight modification, TiCl$_4$ (2.87 mL, 26.2 mmol) was slowly added to a stirred solution of dry THF (60 mL) under argon at 0° C. To the resulting yellow solution was slowly added LiAlH$_4$ (665 mg, 17.5 mmol). The resulting black mixture was stirred at room temperature for 15 min and then triethylamine (23.0 mL, 164 mmol) was added. The black mixture was then poured into a solution of 3 (725 mg, 3.65 mmol) in dry THF (45 mL). The mixture was stirred for 30 min at room temperature and then water (45 mL) was added. The mixture was filtered. The filtrate was extracted with CH$_2$Cl$_2$. The organic layer was dried (Na$_2$SO$_4$) and evaporated under reduced pressure. The resulting yellow oil was purified by chromatography (silica, ethyl acetate) to give a pale yellow oil, which solidified to a pale yellow solid on cooling (448 mg, 65%): mp 53-54° C.; $^1$H NMR δ 0.94 (s, 3H), 1.10 (s, 3H), 2.04 (m, 3H), 2.23-2.42 (m, 2H), 2.54-2.65 (m, 1H), 2.73-2.82 (m, 1H), 3.57-3.68 (m, 1H), 5.90-5.97 (m, 1H), 6.05-6.13 (m, 1H), 6.67-6.73 (m, 1H), 9.70-9.92 (br, 1H); $^{13}$C NMR δ20.3, 22.6, 27.0, 27.9, 41.8, 54.1, 80.1, 105.1, 107.1, 116.3, 131.4, 174.6; FAB-MS obsd 191.1551, calcd 191.1548 (C$_{12}$H$_{18}$N$_2$).

Byproduct (5). To a vigorously stirred solution of 2 (2.00 g, 8.39 mmol) in 40 mL of acetic acid at room temperature, zinc dust (13.7 g, 210 mmol) was added all at once. The reaction mixture was stirred at room temperature for 1 h, and then was filtered through Celite. The filtrate was removed under vacuum and CH$_2$Cl$_2$ (100 mL) was added. The solution was washed with 10% aqueous Na$_2$CO$_3$ (100 mL). The organic layer was separated and chromatographed, affording 3 (143 mg, 8.2%). The aqueous layer was extracted with CH$_2$Cl$_2$ (3×100 mL) and the resulting organic layer was dried (Na$_2$SO$_4$) and concentrated to give a dark pink solid which still contained about 10% of the N-oxide (720 mg). Recrystallization (CHCl$_3$) afforded dark pink crystals (254 mg, 13%). mp 145° C.; $^1$H NMR δ 0.95 (s, 3H), 1.21 (s, 3H), 1.50 (s, 3H), 1.59 (d, J=11.7 Hz, 1H), 1.74 (d, J=11.7 Hz, 1H), 1.83-1.97 (br, 1H), 2.64 (d, J=16.1 Hz, 1H), 2.86 (dd, J=16.1 Hz, 5.1 Hz 1H), 3.36 (d, J=5.1 Hz, 1H), 5.92-5.99 (m, 1H), 6.54-6.60 (m, 1H), 7.72-7.92 (br, 1H); $^{13}$C NMR δ 24.5, 27.3, 28.5, 34.3, 42.0, 58.6, 60.6, 65.4, 103.4, 116.0, 123.6, 129.2; FAB-MS obsd 191.1553, calcd 191.1548 (C$_{12}$H$_{20}$N$_2$).

Two-flask procedure for chlorin formation using AgIO$_3$, exemplified for Zn(II)-17,18-dihydro-18,18-dimethyl-5-(4-methylphenyl)-10-mesitylporphyrin (Zn-8a). Following a general procedure for chlorin formation (Strachan, et al.

(2000) *J. Org. Chem.* 65:3160-3172; Balasubramanian, et al. (2000) *J. Org. Chem.* 65:7919-7929), to a solution of 6a (138 mg, 0.300 mmol) in 10 mL of anhydrous THF/methanol (4:1) was added a 10-fold excess of NaBH$_4$ (113 mg, 3.00 mmol). The reaction was monitored by TLC [silica, hexanes/ethyl acetate (5:1)] and upon completion was carefully quenched with cold water (50 mL), then extracted with distilled CH$_2$Cl$_{12}$ (3×20 mL). The combined organic layers were dried (K$_2$CO$_3$) and concentrated under reduced pressure without heating to afford the carbinol 6a-OH. The residue was dissolved in 3 mL of anhydrous CH$_3$CN. 1,3,3-trimethyl-2,3,4,5-tetrahydrodipyrrin (4) (56.5 mg, 0.300 mmol) was added followed by TFA (23 μL, 0.30 mmol). The solution was stirred at room temperature for 30 min. The reaction was quenched with 10% aqueous NaHCO$_3$ (50 mL) and extracted with distilled CH$_2$Cl$_2$ (3×20 mL). The combined organic layers were washed with water, dried (Na$_2$CO$_3$) and concentrated in vacuo without heating. The residue was dissolved in 30 mL of toluene, to which AgIO$_3$ (1.27 g, 4.50 mmol), Zn(OAc)$_2$ (825 mg, 4.50 mmol) and piperidine (445 μL, 4.50 mmol) were added. The reaction mixture was heated at 80° C. for 2 h. The reaction mixture was concentrated under reduced pressure. Chromatography of the residue [silica, hexanes/CH$_2$Cl$_2$ (2:1)] afforded a blue solid (12 mg, 7%). Analytical data are consistent with literature values (Strachan, et al. (2000) *J. Org. Chem.* 65:3160-3172).

Studies of the Western Half (4)+Eastern Half (6a-OH) Condensation. A sample of 6a (58.5 mg, 100 μmol) was reduced with NaBH$_4$ (37.8 mg, 1.00 mmol) in 2 mL of anhydrous THF/methanol (4:1). The resulting 6a-OH and 4 (18.8 mg, 100 μmol) were dissolved in 10 mL of anhydrous CH$_2$Cl$_2$, then 1 mL portions of the solution were placed in each of 10 vials (each vial contains 10 μmol of 6a-OH and 4). The solvent was evaporated and then 0.1 mL of CH$_3$CN containing the desired TFA concentration (10 to 316 mM) was added. After the desired reaction time (1 min to 2 h), the solution was diluted with 0.9 mL of CH$_3$CN [containing AgTf (7.7 mg, 30 μmol) and 2,2,6-tetramethylpiperidine (25.3 μL, 150 μmol)]. Then Zn(OAc)$_2$ (27.5 mg, 150 μmol) was added and the mixture was refluxed for 4.5 h. The reaction yield was determined by UV-vis spectroscopy. In the yield determinations, CH$_3$CN was added to each reaction mixture to bring the volume to 4.0 mL (thereby negating any possible error due to solvent evaporation during the reflux period). A 25 μL aliquot was then removed and transferred to a 4 mL cuvette (containing toluene). Quantitation was then based on the absorption at 609 nm ($\epsilon_{609}$=43,600 M$^{-1}$cm$^{-1}$).

1,3,3-Trimethyl-10-(4-methylphenyl)-15-mesityl-19-bromo-2,3,4,5-tetrahydrobilene-α (7a). Following a general procedure, treatment of 6a (585 mg, 1.00 mmol) with NaBH$_4$ (370 mg, 10.0 mmol) in 20 mL of anhydrous THF/methanol (4:1) afforded 6a-OH. The sample of 6a-OH was dissolved in 10 mL of anhydrous CH$_3$CN, then 4 (188 mg, 1.00 mmol) and TFA (77 μL, 1.0 mmol) were added. The reaction mixture was stirred at room temperature for 30 min. Then 10% aqueous NaHCO$_3$ (50 mL) was added and the mixture was extracted with distilled CH$_2$Cl$_2$ (3×20 mL). The combined organic layers were washed with water, dried (Na$_2$CO$_3$) and concentrated in vacuo without heating. The resulting brown solid was purified by chromatography [silica, hexanes/ethyl acetate (5:1), and then ethyl acetate] to give a brown solid (460 mg, 72%): mp 67-70° C.; $^1$H NMR δ 0.90 (s, 3H), 1.07 (s, 3H), 1.91 (s, 3H), 2.04 (s, 6H), 2.25 (s, 3H), 2.26-2.30 (m, 2H), 2.31 (s, 3H), 2.48-2.60 (m, 1H), 2.66-2.72 (m, 1H), 3.52-3.63 (m, 1H), 5.28-5.32 (m, 1H), 5.67-5.81 (m, 6H), 6.00-6.04 (m, 1H), 6.81 (s, 1H), 7.06-7.11 (m, 4H), 7.67-7.79 (br, 1H), 7.99-8.13 (br, 1H), 9.23-9.32 (br, 1H); FAB-MS obsd 635.2749, calcd 635.2730 (C$_{38}$H$_{43}$BrN$_4$).

Studies of the Metal-Mediated Oxidative Cyclization. A solution of tetrahydrobilene 7a (63.5 mg, 100 μmol) in 10 mL of anhydrous CH$_2$Cl$_2$ was divided into 0.5 mL portions in each of 20 vials (each vial contains 5 μmol of 7a). For the study examining the effect of the reaction solvent, CH$_2$Cl$_2$ was then evaporated, and 0.5 mL of the solvent of interest was added. The corresponding reagents for the oxidation [2,2,6,6-tetramethylpiperidine (13 μL, 77 μmol) and Zn(OAc)$_2$ (14 mg, 76 μmol)] were added and the mixture was refluxed for 4.5 h. The yield of chlorin was determined by UV-vis spectroscopy. In the yield determinations, CH$_2$Cl$_2$ was added to each reaction mixture to bring the volume to 4.0 mL (thereby negating any possible error due to solvent evaporation during the reflux period). A 50 μL aliquot was then removed and transferred to a 4 mL cuvette (containing toluene). Quantitation was then based on the absorption at 609 nm ($\epsilon_{609}$=43,600 M$^{-1}$cm$^{-1}$).

Two-flask procedure for chlorin formation, exemplified for Zn(II)-17,18-dihydro-18,18-dimethyl-5-(4-methylphenyl)-10-mesitylporphyrin (Zn-8a). A solution of 7a (75.8 mg, 0.120 mmol) in CH$_3$CN (12 mL) was treated with Zn(OAc)$_2$ (328 mg, 1.79 mmol), AgTf (91.9 mg, 0.360 mmol) and 2,2,6,6-tetramethylpiperidine (300 μL, 1.79-mmol). The reaction mixture was refluxed for 24 h. The reaction mixture was concentrated under reduced pressure, and then the residue was chromatographed [silica, hexanes/CH$_2$Cl$_2$ (2:1)] to give a blue solid (45 mg, 62%). Analytical data are consistent with literature values (Strachan, et al. (2000) *J. Org. Chem.* 65:3160-3172).

One-flask procedure for chlorin formation, exemplified for Zn(II)-17,18-dihydro-18,18-dimethyl-5-(4-methylphenyl)-10-mesitylporphyrin (Zn-8a). Following a general procedure, treatment of 6a (231 mg, 0.500mmol) with NaBH$_4$ (185 mg, 5.00 mmol) in 20 mL of anhydrous THF/methanol (4:1) afforded 6a-OH. The sample of 6a-OH was dissolved in 5 mL of anhydrous CH$_3$CN, then 4 (94 mg, 0.50 mmol) and TFA (39 μL, 0.50 mmol) were added. The reaction mixture was stirred at room temperature for 30 min, then the reaction mixture was diluted with 45 mL of CH$_3$CN. AgTf (385 mg, 1.50 mmol), Zn(OAc)$_2$ (1.38 g, 7.50 mmol) and 2,2,6,6-tetramethylpiperidine (2.53 mL, 15.0 mmol, 30 mol equiv) were added. The resulting mixture was refluxed for 18 h. The reaction mixture was concentrated under reduced pressure. The residue was chromatographed [silica, hexanes/CH$_2$Cl$_2$ (2:1)], affording a blue solid (118 mg, 31%). Analytical data are consistent with literature values (Strachan, et al. (2000) *J. Org. Chem.* 65:3160-34172).

S-2-Pyridyl 3,5-di-tert-butylbenzothioate (11). To a stirred solution of 2-mercaptopyridine (2.78 g, 25.0 mmol) in CH$_2$Cl$_2$ (50 mL) was added a solution of 3,5-di-tert-butylbenzoyl chloride (6.31 g, 25.0 mmol) in CH$_2$Cl$_2$ (125 mL) over 10 min. After 5 h, TLC showed complete consumption of the 2-mercaptopyridine, then 2 N NaOH was added. The organic phase was isolated, washed with water, then dried (Na$_2$SO$_4$) and the solvent was removed to afford a white solid. The solid was recrystallized in hexane affording a white solid (5.05 g, 62%): mp 73-74° C.; $^1$H NMR δ 1.36 (s, 18H), 7.31-7.36 (m, 1H), 7.67-7.70 (m, 1H), 7.75-7.80 (m, 2H), 7.85-7.88 (m, 2H), 8.66-8.69 (m, 1H); $^{13}$C NMR δ 32.0, 35.7, 122.6, 124.2, 128.9, 131.4, 136.9, 137.7, 151.1, 152.3, 152.5, 190.8; Anal. Calcd for C$_{20}$H$_{25}$NOS: C, 73.35; H, 7.69; N, 4.28. Found: C, 73.40; H, 7.75; N, 4.23.

1-(4-Methylbenzoyl)-5-{4-[2 -(trimethylsilyl)ethoxycarbonyl]phenyl}dipyrromethane (13c). Following the general procedure (Rao, et al. (2000) *J. Org. Chem.* 65:1084-1092), EtMgBr (13.1 mL, 13.1 mmol), 1.0 M in THF) was added to a solution of 9c (2.00 g, 5.46 mmol) in dry THF (10 mL) at room temperature under argon. The mixture was stirred at room temperature for 10 min and then cooled to −78° C. A solution of S-2-pyridyl 4-methylbenzothioate (10) (1.25 g, 5.45 mmol) in dry THF (10 mL) was added. The reaction mixture was maintained at −78° C. for 10 min, then the cooling bath was removed. After 3 h, the reaction was quenched with 100 mL of saturated aqueous $NH_4Cl$. The reaction mixture was extracted with $CH_2Cl_2$, washed with water, and then dried ($Na_2SO_4$) and concentrated under reduced pressure to give a dark foam. Column chromatography [silica packed with hexanes/ethyl acetate (10:1), eluted with hexanes/ethyl acetate (5:1)] afforded a golden amorphous solid (1.42 g, 54%): mp 67-70° C.; $^1$H NMR δ 0.07 (s, 9H), 1.11 (t, J=8.1 Hz, 2H), 2.42 (s, 3H), 4.39 (t, J=8.1 Hz, 2H), 5.62 (s, 1H), 5.95-5.99 (m, 1H), 6.06-6.10 (m, 1H), 6.12-6.16 (m, 1H), 6.64-6.68 (m, 1H), 6.77-6.81 (m, 1H), 7.16-7.30 (m, 4H), 7.67 (d, J=7.3 Hz, 2H), 7.89 (d, J=7.3 Hz, 2H), 8.52-8.68 (br, 1H), 10.30-10.42 (br, 1H); $^{13}$C NMR δ −0.8, 18.0, 22.2, 44.6, 63.9, 108.6, 109.0, 111.3, 118.7, 121.4, 128.9, 129.6, 129.7, 130.1, 130.4,. 130.8, 131.6, 136.1, 141.4, 143.1, 146.5, 167.1, 185.3; Anal. Calcd for $C_{29}H_{32}N_2O_3Si$: C, 71.87; H, 6.65; N, 5.78. Found: C, 71.78; H, 6.61; N, 5.89.

1-(3,5-Di-tert-butylbenzoyl)-5-(4-iodophenyl)dipyrromethane (13d). Following the general procedure (Rao, et al. (2000) *J. Org. Chem.* 65(4):1084-1092), reaction of 9d (1.80 g, 5.10 mmol) and 11 (1.70 g, 5.10 mmol) followed by column chromatography [silica hexanes/ethyl acetate (5:1)] afforded a golden amorphous solid (1.63 g, 56%): mp 119-120° C.; $^1$H NMR δ 1.34 (s, 18H), 5.51 (s, 1H), 5.93-5.97 (m, 1H), 6.07-6.14 (m, 2H), 6.57-6.63 (m, 1H), 6.73-6.77 (m, 1H), 6.92 (d, J=8.1 Hz, 2H), 7.49 (d, J=8.1 Hz, 2H), 7.60-7.67 (m, 3H), 8.57-8.70 (br, 1H), 10.38-10.52 (br, 1H); $^{13}$C NMR δ 32.1, 35.6, 44.4, 93.3, 108.1, 108.5, 109.1, 111.3, 118.1, 118.8, 121.8, 124.1, 126.7, 130.9, 131.9, 138.3, 141.4, 141.8, 151.5, 186.6; Anal. Calcd for $C_{30}H_{33}IN_2O$: C, 63.83; H, 5.89; N, 4.96. Found: C, 63.59; H, 5.95; N, 4.83.

1-(3,5-Di-tert-butylbenzoyl)-5-{4-[2-(trimethylsilyl)ethynyl]phenyl}dipyrromethane (13e). Following the general procedure (Rao, et al. (2000) *J. Org. Chem.* 65(4):1084-1092), reaction of 9e (2.00 g, 6.28 mmol) and 11 (2.06 g, 6.28 mmol) followed by column chromatography [silica hexanes/ethyl acetate (5:1)] afforded a golden amorphous solid (2.00 g, 60%): mp 108° C. (dec.) $^1$H NMR δ0.23 (s, 9H), 1.34 (s, 18H), 5.57 (s, 1H), 5.93-5.97 (m, 1H), 6.06-6.16 (m, 2H), 6.58-6.62 (m, 1H), 6.75-6.80 (m, 1H), 7.10 (d, J=8.1 Hz, 2H), 7.28 (d, J=8.1 Hz, 2H), 7.60-7.68 (m, 3H), 8.62-8.70 (br, 1H), 10.45-10.52 (br, 1H); $^{13}$C NMR δ0.7, 32.1, 35.6, 44.7, 94.9, 105.6, 108.4, 108.9, 111.4, 118.8, 122.1, 122.5, 124.2, 126.7, 128.9, 131.3, 131.8, 132.8, 138.4, 142.1, 142.4, 151.5, 186.8; Anal. Calcd for $C_{35}H_{42}N_2OSi$: C, 78.60; H, 7.92; N, 5.24. Found: C, 78.75; H, 7.96; N, 5.20.

1-Bromo-9-(4-methylbenzoyl)-5-{4-[2-(trimethylsilyl)ethoxycarbonyl]phenyl}dipyrromethane (6c). Following the general procedure (Strachan, et al. (2000) *J. Org. Chem.* 65:3160-3172; Balasubramanian, et al. (2000) *J. Org. Chem.* 65:7919-7929), a solution of 13c (470 mg, 0.970 mmol) in 25 mL of dry THF was cooled to −78° C. under argon. NBS (173 mg, 0.970 mmol) was added, and the reaction mixture was stirred for 1 h at −78° C. Hexanes (50 mL) and water (50 mL) were added and the mixture was allowed to warm to room temperature. The organic phase was extracted with $CH_2Cl_2$ and dried ($Na_2SO_4$) and the solvent was removed under reduced pressure without heating. Column chromatography [silica; hexanes/ethyl acetate (4:1)] afforded a light brown powder (444 mg, 81%): mp 152° C. (dec.); $^1$H NMR δ 0.07 (s, 9H), 1.11 (t, J=8.1 Hz, 2H), 2.16 (s, 3H), 4.39 (t, J=8.1 Hz, 2H), 5.57 (s, 1H), 5.89-5.93 (m, 1H), 6.02-6.06 (m, 1H), 6.09-6.13 (m, 1H), 6.76-6.80 (m, 1H), 7.17 (d, J=8.1 Hz, 2H), 7.23 (d, J=8.1 Hz, 2H), 7.60 (d, J=8.1 Hz, 2H), 7.84 (d, J=8.1 Hz, 2H), 9.10-9.26 (br, 1H), 10.82-10.94 (br, 1H); $^{13}$C NMR δ −0.9, 17.9, 22.2, 44.6, 63.8, 98.8, 105.0, 110.4, 110.8, 111.2, 122.1, 128.7, 129.5, 129.8, 130.1, 130.3, 131.7, 132.4, 141.2, 143.2, 145.9, 167.0, 185.7; Anal. Calcd for $C_{29}H_{31}BrN_2O_3Si$: C, 61.81; H, 5.54; N, 4.97. Found: C, 61.96; H, 5.53; N, 4.93.

1-Bromo-9-(3,5-di-tert-butylbenzoyl)-5-(4-iodophenyl)dipyrromethane (6d). Following the general procedure outlined for the synthesis of 6c, reaction of 13d (800 mg, 1.42 mmol) with NBS (253 mg, 1.42 mmol) followed by column chromatography [silica hexanes/ethyl acetate (4:1)] afforded a light brown powder (770 mg, 84%): mp 88-91° C.; $^1$H NMR δ 1.34 (s, 18H), 5.51 (s, 1H), 5.89 (t, J=2.9 Hz, 1H), 6.03 (t, J=2.9Hz, 1H), 6.11 (t, J=2.9 Hz, 1H), 6.77 (t, J=2.9 Hz, 1H), 6.96 (d, J=8.1 Hz, 2H), 7.51 (d, J=8.1 Hz, 2H), 7.62 (s, 3H), 8.91-9.00 (br, 1H), 10.59-10.72 (br, 1H); $^{13}$C NMR δ 32.1, 35.6, 44.5, 93.5, 98.8, 110.4, 111.1, 111.4, 122.2, 124.2, 126.9, 130.9, 132.0, 132.6, 138.2, 138.4, 140.7, 141.3, 151.6, 187.0; Anal. Calcd for $C_{30}H_{32}BrIN_2O$: C, 56.00; H, 5.01; N, 4.35. Found: C, 56.15; H, 5.19; N, 4.22.

1-Bromo-9-(3,5-di-tert-butylbenzoyl)-5-{4-[2-(trimethylsilyl)ethynyl]phenyl}dipyrromethane (6e). Following the general procedure outlined for the synthesis of 6c, reaction of 13e (1.00 g, 1.87 mmol) with NBS (333 mg, 1.87 mmol) followed by column chromatography [silica hexanes/ethyl acetate (5:1)] afforded a golden amorphous solid (914 mg, 80%): mp 118° C. (dec.); $^1$H NMR δ 0.23 (s, 9H), 1.33 (s, 18H), 5.56 (s, 1H), 5.86-5.91 (m, 1H), 6.01-6.04 (m, 1H), 6.08-6.12 (m, 1H), 6.74-6.79 (m, 1H), 7.15 (d, J=8.1 Hz, 2H), 7.29 (d, J=8.1 Hz, 2H), 7.58-7.67 (m, 3H), 8.94-9.06 (br, 1H), 10.62-10.76 (br, 1H); $^{13}$C NMR δ 0.6, 32.1, 35.6, 44.8, 95.3, 98.7, 105.3, 110.3, 111.1, 111.4, 122.0, 122.8, 124.2, 126.7, 128.8, 131.9, 132.7, 132.9, 138.3, 141.2, 141.3, 151.5, 186.9; Anal. Calcd for $C_{35}H_{41}BrN_2OSi$: C, 68.50; H, 6.73; N, 4.56. Found: C, 68.48; H, 6.87; N, 4.47.

1,3,3-Trimethyl-10,15-bis(pentafluorophenyl)-19-bromo-2,3,4,5-tetrahydrobilene-α (7b). Following the general procedure, treatment of 6b (176 mg, 0.300 mmol) with $NaBH_4$ (113 mg, 3.00 mmol) in 10 mL of anhydrous THF/methanol (4:1) afforded 6b-OH. The reaction of 6b-OH and 4 (57 mg, 0.30 mmol) in 3 mL of anhydrous $CH_3CN$ containing TFA (23 μL, 0.30 mmol) for 30 min followed by the standard workup afforded a brown solid (73 mg, 32%): mp 56-58° C.; $^1$H NMR δ 0.90 (s, 3H), 1.11 (s, 3H), 1.92 (s, 3H), 2.23-2.42 (m, 2H), 2.50-2.72 (m, 2H), 3.52-3.62 (m, 1H), 5.73-6.08 (m, 8H), 8.27-8.46 (br, 1H), 8.58-8.70 (br, 1H), 9.72-9.85 (br, 1H); Anal. Calcd for $C_{34}H_{25}BrF_{10}N_4$: C, 53.77; H; 3.32; N, 7.38. Found: C, 53.51; H, 3.41; N, 6.97; FAB-MS obsd 759.1181, calcd 759.1215 ($C_{34}H_{25}BrF_{10}N_4$).

Zn(II)-17,18-Dihydro-18,18-dimethyl-5,10-bis(pentafluorophenyl)porphyrin (Zn-8b). A solution of 7b (77.7 mg, 0.102 mmol) in $CH_3CN$ (10 mL) containing the oxidative cyclization reagents was refluxed for 24 h. Standard workup and chromatography [silica, hexanes/$CH_2Cl_2$ (2:1)] gave a greenish blue solid (28.2 mg, 38%). Analytical data are consistent with literature values (Strachan, et al. (2000) *J. Org. Chem.* 65:3160-3172).

1,3,3-Trimethyl-10-(4-methylphenyl)-15-{4-[2-(trimethylsilyl)ethoxycarbonyl]phenyl}-19-bromo-2,3,4,5-tetrahydrobilene-α (7c). Following the general procedure, treatment of 6c (282 mg, 0.500 mmol) with $NaBH_4$ (189 mg, 5.00 mmol) in 30 mL of anhydrous THF/methanol (4:1) afforded 6c-OH. The reaction of 6c-OH and 4 (94 mg, 0.50 mmol) in 5 mL of anhydrous CH$_3$CN with TFA (39 μL, 0.50 mmol) for 30 min followed by the standard workup afforded a brown solid (203 mg, 55%): mp 81-83° C.; $^1$H NMR δ 0.14 (s, 9H), 0.96 (s, 3H), 1.14 (s, 3H), -1.15 (t, J=8.1 Hz, 2H), 1.92-1.97 (m, 3H), 2.24-2.43 (m, 2H), 2.38 (s, 3H), 2.53-2.67 (m, 1H), 2.71-2.80 (m, 1H), 3.57-3.68 (m, 1H), 4.47 (t, J=8.1 Hz, 2H), 5.32-5.43 (m, 2H), 5.72-5.84 (m, 4H), 5.84-5.90 (m, 1H), 6.05-6.10 (m, 1H), 7.10-7.18 (m, 4H), 7.24-7.34 (m, 2H), 7.90-8.06 (m, 1H), 7.96-8.04 (m, 2H), 8.21-8.46 (m, 1H), 9.23-9.36 (m, 1H); FAB-MS obsd 737.2907, calcd 737.2886 (C$_{41}$H$_{49}$BrN$_4$O$_2$Si).

Zn(II)-17,18-Dihydro-18,18-dimethyl-5-(4-methylphenyl)-10-[4-[2-(trimethylsilyl)ethoxycarbonyl]phenyl]porphyrin (Zn-8c). A solution of 7c (110 mg, 0.150 mmol) in CH$_3$CN (15 mL) containing the oxidative cyclization reagents was refluxed for 14 h. Standard workup and chromatography [silica, hexanes/CH$_2$Cl$_2$ (1:2)] gave a blue solid (43 mg, 41%): $^1$H NMR δ 0.18 (s, 9H), 1.12 (t, J=5.5 Hz, 2H), 2.03 (s, 6H), 2.66 (s, 3H), 4.52 (s, 2H), 4.65 (t, J=5.5 Hz, 2H), 7.48 (d, J=8.1 Hz, 2H), 7.94 (d, J=8.1 Hz, 2H), 8.13 (d, J=8.1 Hz, 2H), 8.31 (d, J=4.4 Hz, 1H), 8.34 (d, J=8.1 Hz, 2H), 8.42 (d, J=4.4 Hz, 1H), 8.57-8.70 (m, 6H); LD-MS obsd 710.78; FAB-MS obsd 712.2232, calcd 712.2212 (C$_{41}$H$_{40}$N$_4$O$_2$SiZn); λ$_{abs}$ (toluene) 413, 609 nm.

1,3,3-Trimethyl-10-(3,5-di-tert-butylphenyl)-15-(4-iodophenyl)-19-bromo-2,3,4,5-tetrahydrobilene-α (7d). Following the procedure, treatment of 6d (322 mg, 0.500 mmol) with NaBH$_4$ (189 mg, 5.00 mmol) in 30 mL of anhydrous THF/methanol (4:1) afforded 6d-OH. The reaction of 6d-OH and 4 (94 mg, 0.50 mmol) in 5 mL of anhydrous CH$_3$CN containing TFA (39 μL, 0.50 mmol) followed by standard workup afforded a brown solid (163 mg, 40%): mp 70-73° C.; $^1$H NMR δ 0.91 (s, 3H), 1.06 (s, 3H), 1.25 (s, 18H), 1.83-1.87 (m, 3H), 2.17-2.34 (m, 2H), 2.51-2.62 (m, 1H), 2.66-2.76 (m, 1H), 3.52-3.59 (m, 1H), 5.22-5.27 (m, 1H), 5.29-5.35 (m, 1H), 5.66-5.88 (m, 5H), 5.97-6.03 (m, 1H), 6.87-6.93 (m, 2H), 7.00-7.07 (m, 3H), 7.54-7.62 (m, 2H), 7.79-7.94 (m, 1H), 8.08-8.28 (m, 1H), 9.08-9.22 (m, 1H), Anal. Calcd for C$_{42}$H$_{50}$BrIN$_4$: C, 61.69; H, 6.16; N, 6.85. Found: C, 61.57; H, 6.21; N, 6.70; FAB-MS obsd 817.2317, calcd 817.2342 (C$_{42}$H$_{50}$BrIN$_4$).

Zn(II)-17,18-Dihydro-18,18-dimethyl-5-(3,5-di-tert-butylphenyl)-10-(4-iodophenyl)porphyrin (Zn-8d). A solution of 7d (81.7 mg, 0.100 mmol) in CH$_3$CN (10 mL) containing the oxidative cyclization reagents was refluxed for 20 h. Standard workup and chromatography [silica, hexanes/CH$_2$Cl$_2$ (1:2)] gave a blue solid (32 mg, 40%): $^1$H NMR δ 1.49 (s, 18H), 2.03 (s, 6H), 4.51 (s, 2H), 7.72 (t, J=1.5 Hz, 1H), 7.80 (d, J=8.1 Hz, 2H), 7.89-7.93 (m, 2H), 8.01 (d, J=8.1 Hz, 2H), 8.35 (d, J=4.5 Hz, 1H), 8.44 (d, J=4.5 Hz, 1H), 8.58 (s, 1H), 8.61-8.63 (m, 2H), 8.65-8.69 (m, 2H), 8.70-8.74 (m, 1H); LD-MS obsd 791.60; FAB-MS obsd 792.1667, calcd 792.1689 (C$_{42}$H$_{41}$IN$_4$Zn); λ$_{abs}$ (toluene) 412, 609 nm.

1,3,3-Trimethyl-10-(3,5-di-tert-butylphenyl)-15-{4-[2-(trimethylsilyl)ethynyl]phenyl}-19-bromo-2,3,4,5-tetrahydrobilene-α (7e). Following the general procedure, treatment of 6e (307 mg, 0.500 mmol) with NaBH$_4$ (189 mg, 5.00 mmol) in 30 mL of anhydrous THF/methanol (4:1) afforded 6e-OH. The reaction of 6e-OH and 4 (94 mg, 0.50 mmol) in 5 mL of anhydrous CH$_3$CN containing TFA (39 μL, 0.50 mmol) followed by the standard workup afforded a brown solid (233 mg, 59%): mp 61-63° C.; $^1$H NMR δ 0.24 (s, 9H), 0.90 (s, 3H), 1.06 (s, 3H), 1.25 (s, 18H), 1.83-1.90 (m, 3H), 2.21-2.47 (m, 2H), 2.49-2.62 (m, 1H), 2.66-2.75 (m, 1H), 3.51-3.60 (m, 1H), 5.25-5.3$_5$ (m, 1H), 5.65-5.88 (m, 5H), 5.96-6.02 (m, 1H), 6.97-7.04 (m, 3H), 7.04-7.14 (m, 2H), 7.32-7.42 (m, 2H), 7.81-7.96 (m, 1H), 8.07-8.21 (m, 1H), 9.08-9.20 (m, 1H); FAB-MS obsd 787.3802, calcd 787.3771 (C$_{47}$H$_{59}$BrN$_4$Si).

Zn(II)-17,18-dihydro-18,18-dimethyl-5-(3,5-di-tert-butylphenyl)-10-(4-ethynyl]phenyl)porphyrin (Zn-8e). A solution of 7e (118 mg, 0.150 mmol) in CH$_3$CN (15 mL) containing the oxidative cyclization reagents was refluxed for 12 h. Standard workup and chromatography [silica, hexanes/CH$_2$Cl$_2$ (2:1)] gave a blue solid (28 mg, 27%). Deprotection of the trimethylsilylethyne apparently occurred under these conditions: $^1$H NMR δ 1.49 (s, 18H), 2.02 (s, 6H), 3.26 (s, 1H), 4.50 (s, 2H), 7.71-7.74 (m, 1H), 7.81 (d, J=8.1 Hz, 2H), 7.90-7.94 (m, 2H), 8.03 (d, J=8.1 Hz, 2H), 8.35 (d, J=4.5 Hz, 1H), 8.45 (d, J=4.5 Hz, 1H), 8.58 (s, 1H), 8.59-8.62 (m, 2H), 8.63-8.68 (m, 2H), 8.72 (d, J=4.5 Hz, 1H); LD-MS obsd 689.45; FAB-MS obsd 690.2748, calcd 690.2701 (C$_{44}$H$_{42}$N$_4$Zn); λ$_{abs}$ (toluene) 413, 609 nm.

1,3,3-Trimethyl-10-(4-methylphenyl)-15-{4-[2-(trimethylsilyl)ethynyl]phenyl}-19-bromo-2,3,4,5-tetrahydrobilene-α (7f). Treatment of 6f (309 mg, 0.600 mmol) with NaBH$_4$ (226 mg, 6.00 mmol) in 40 mL of anhydrous THF/methanol (4:1) afforded 6f-OH. The reaction of 6f-OH and 4 (113 mg, 0.600 mmol) in 6 mL of anhydrous CH$_3$CN containing TFA (46 μL, 0.60 mmol) followed by the standard workup afforded a brown solid (273 mg, 66%): mp 77-79° C.; $^1$H NMR δ 0.27 (s, 9H), 0.90 (s, 3H), 1.08 (s, 3H), 1.85 (s, 3H), 2.27-2.31 (m, 2H), 2.32 (s, 3H), 2.49-2.57 (m, 1H), 2.66-2.71 (m, 1H), 3.52-3.56 (m, 1H), 5.23-5.27 (m, 2H), 5.68-5.72 (m, 4H), 5.80-5.84 (m, 1H), 5.99-6.03 (m, 1H), 7.05-7.07 (m, 2H), 7.07-7.10 (m, 4H), 7.35-7.39 (m, 2H), 7.84-7.96 (m, 1H), 8.16-8.37 (m, 1H), 9.16-9.28 (m, 1H); Anal. Calcd for C$_{40}$H$_{45}$BrN$_4$Si: C, 69.65; H, 6.58; N, 8.12. Found: C, 69.17; H, 6.69; N, 7.74; FAB-MS obsd 689.2713, calcd 689.2675 (C$_{40}$H$_{45}$BrN$_4$Si).

Zn(II)-17,18-Dihydro-18,18-dimethyl-5-(4-methylphenyl)-10-(4-ethynyl]phenyl)porphyrin (Zn-8f). A solution of 7f (158 mg, 0.229 mmol) in THF (23 mL) containing the oxidative cyclization reagents was refluxed for 24 h. Standard workup and chromatography [silica, hexanes/CH$_2$Cl$_2$ (2:1)] gave a greenish blue solid (61 mg, 45%). Deprotection of the trimethylsilylethyne apparently occurred under these conditions: $^1$H NMR δ 2.03 (s, 6H), 2.66 (s, 3H), 3.27 (s, 1H), 4.51 (s, 2H), 7.48 (d, J=8.1 Hz, 2H), 7.81 (d, J=8.1 Hz, 2H), 7.94 (d, J=8.1 Hz, 2H), 8.03 (d, J=8.1 Hz, 2H), 8.34 (d, J=4.5 Hz, 1H), 8.41 (d, J=4.5 Hz, 1H), 8.58 (s, 1H), 8.60-8.64 (m, 2H), 8.65 (d, J=4.5 Hz, 1H), 8.66 (s, 1H), 8.69 (d, J=4.5 Hz, 1H); LD-MS obsd 591.68; FAB-MS obsd 592.1620, calcd 592.1605 (C$_{37}$H$_{28}$N$_4$Zn); λ$_{abs}$ 413, 609 nm.

Conclusions. We have refined a number of steps in the synthesis of meso-substituted chlorin building blocks. The prior synthesis established a general route to chlorins with defined patterns of functional group handles at the perimeter of the macrocycle. The weaknesses of the prior synthesis included (1) yields of chlorin in the 6-24% range and amounts of chlorin typically in the 5-20 mg range; (2) very short shelf life of the Western half (a dihydrodipyrrin); (3) inability to isolate; characterize, or quantitate the putative dihydrobilene-a intermediate; (4) the use of AgIO$_3$ in the oxidation method which upon prolonged exposure to the reaction mixture resulted in iodinated chlorin byproducts. The refined method described herein affords a stable Western half (a tetrahydrodipyrrin) in good yield. The Western half undergoes smooth condensation with the Eastern half, affording a stable tetrahydrobilene-α intermediate. Studies of the conversion of the latter to the chlorin revealed simple reaction conditions [AgTf, Zn(OAc)$_2$, and 2,2,6,6,-tetramethylpiperidine in CH$_3$CN at reflux exposed to air] that proceed in a clean manner and in good yield. A one-flask synthetic procedure for chlorin formation has been developed. Using the two-flask procedure, several zinc chlorins were synthesized in yields of 16-45% (based on the Eastern and Western half precursors) and in quantities of 27-118 mg. The isolation of the intermediate tetrahydrobilene-α in each case enabled determination of the yield of the condensation of Eastern and Western halves as well as of the oxidative cyclization of the tetrahydrobilene-α yielding the zinc chlorin.

EXAMPLE 2

Refined Synthesis of β-Substituted Chlorin Building Blocks

In this Example, we have employed this refined route to prepare a β-substituted chlorin that bears an ethyne group and an iodo group in diametrically substituted positions, as well as a 3,5-di-tert-butyl group at one meso position to impart increased solubility in organic solvents. This building block is ideally suited for use in the synthesis of linear multi-chlorin arrays analogous to our multi-porphyrin based molecular wires (Wagner and Lindsey (1994) *J. Am. Chem. Soc.* 116: 9759-9760). The synthesis of such trans-β-substituted chlorin building blocks requires the synthesis of β-substituted Eastern and Western halves.

Synthesis of Substituted Tetrahydrodipyrrin Western Halves. A critical step in the synthesis of the unsubstituted tetrahydrodipyrrin Western half (4) is the deoxygenation of the N-oxide. A Western half bearing a synthetic handle at the β-position provides a convenient entry into β-substituted chlorins (Balasubramanian, et al. (2000) *J. Org. Chem.* 65:7919-7929). We recently developed a route to a β-substituted dihydrodipyrrin Western half (Balasubramanian, et al. (2000) *J. Org. Chem.* 65:7919-7929), which was used herein with modification to obtain the β-substituted tetrahydrodipyrrin counterpart. The requisite iodophenyl-substituted nitrohexanone pyrrole 14 was readily prepared from 3-(4-iodophenyl)pyrrole. Subsequent formylation affords two products due to substitution at either the α- or α'-position; a distinction between the two products is essential because the two patterns of substitution ultimately yield chlorin building blocks with substitution at different β-positions. Such distinction is difficult by $^1$H NMR spectroscopy (Balasubramanian, et al. (2000) *J. Org. Chem.* 65:7919-7929). The remainder of the synthesis of 14 proceeds as for that of 1 (aldol condensation with nitromethane, reduction with NaBH4, Michael addition with mesityl oxide). Reductive cyclization of 14 in the presence of Zn/AcOH gave the N-oxide 15 in 43% yield (Scheme 5). An X-ray structure obtained of 15 confirmed the substitution pattern, thereby eliminating any ambiguity concerning the NMR interpretation of the formylated pyrrole precursor (EXAMPLE 3). This structure also confirms the assigned substitution pattern of the dipyrromethane derivatives that serve as the Eastern half, because the same formylated pyrrole precursor to 14 is employed to prepare the β-substituted Eastern half (vide infra). Deoxygenation of the N-oxide: 15 yielded the β-substituted tetrahydrodipyrrin Western half 16 in 38% yield (Scheme 5). Sonogashira coupling of 16 with (trimethylsilyl)acetylene afforded the trimethylsilylethynyl substituted Western half 17 in 76% yield.

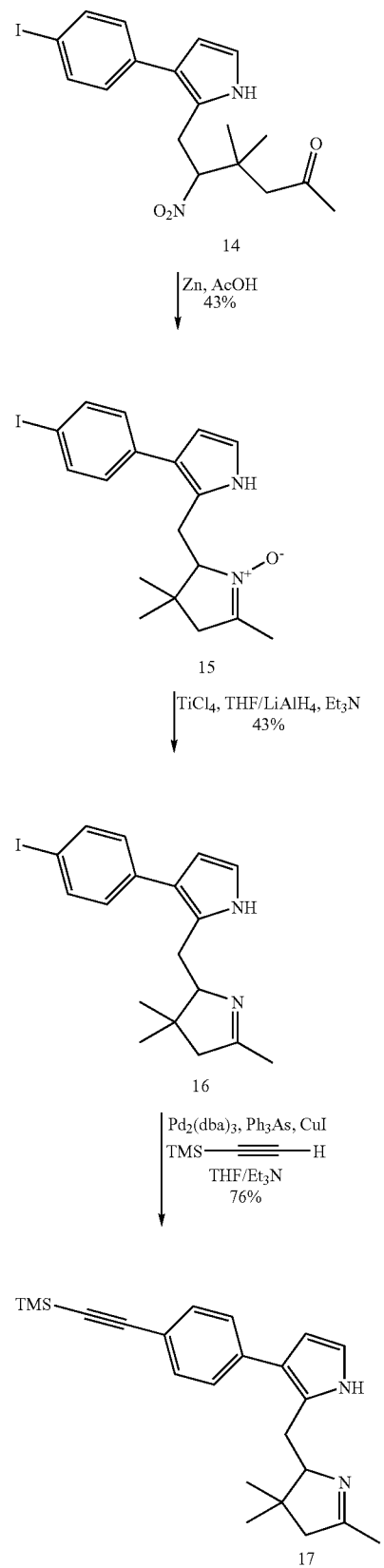

Synthesis of Eastern Halves. The synthesis of the β-substituted Eastern half began in the same manner as our prior synthesis of β-substituted dipyrromethanes (Balasubramanian and Lindsey (1999) *Tetrahedron* 55:6771-6784). A BOC-protected dipyrromethane (18) was obtained from 2-formyl-3-(4-iodophenyl)pyrrole through the protection of the pyrrolic nitrogen, reduction of the aldehyde and condensation with pyrrole. Treatment of BOC-protected dipyrromethane with 3.0 equiv of EtMgBr in THF followed by 3,5-di-tert-butylbenzoyl chloride afforded the monoacylated dipyrromethane 19 in 45% yield (Scheme 6). In this acylation step, we employed 3,5-di-tert-butylbenzoyl chloride instead of p-toluoyl chloride to improve the solubility of the resulting chlorin in organic solvents. Removal of the BOC group under standard conditions (Hasun, et al. (1981) *J. Org. Chem.* 46:157-164) gave 3-(4-iodophenyl)-9-(3,5-di-tert-butylbenzoyl)dipyrromethane (20). Sonogashira coupling (Sonogashira, et al. (1975) *Tetrahedron Lett.* (50):4467-4470) of 20 with (trimethylsilyl)acetylene afforded trimethylsilylethynyl dipyrromethane 21 in 82% yield. Reaction of 21 with NBS at −78° C. gave the corresponding monobromo monoacyl dipyrromethane 22 in 72% yield. Compound 22 serves as the precursor to the Eastern half 22-OH.

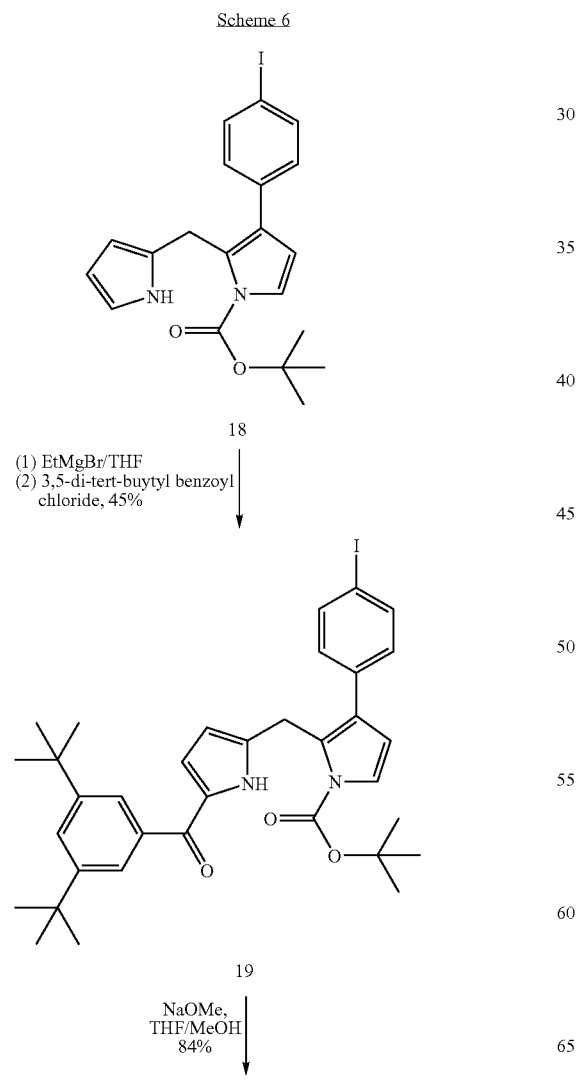

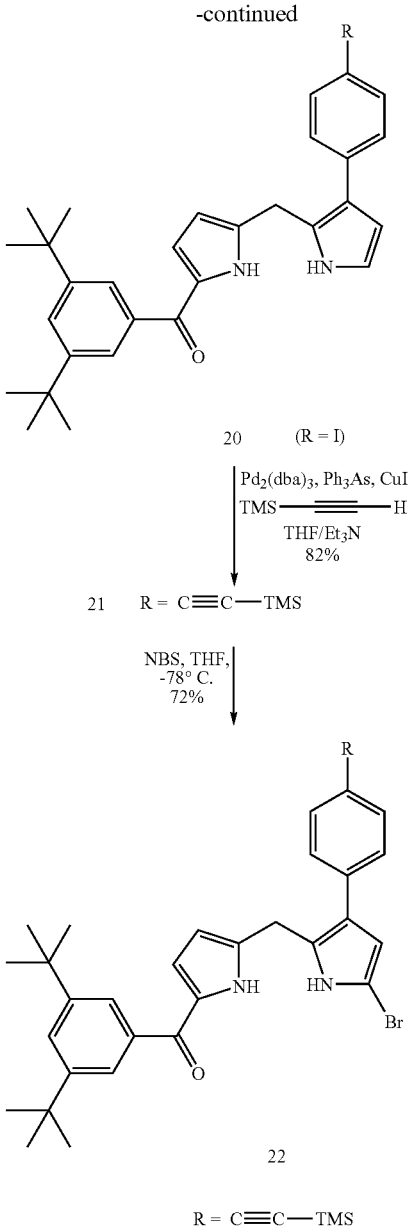

New Chlorins. Chlorins bearing synthetic handles at defined locations at the perimeter of the macrocycle are valuable building blocks for the construction of model systems in biomimetic or materials chemistry. Porphyrinic pigments bearing an ethyne group and an iodo group at diametrically opposed positions are particularly attractive for the construction of linear multiporphyrin arrays (Wagner, et al. (1996) *J. Am. Chem. Soc.* 118:11166-11180). We have found that the extent of electronic communication between porphyrins of a given electronic composition depends on the site of attachment of a linker on the macrocycle (Strachan, et al. (1997) *J. Am. Chem. Soc.* 119:11191-11201; Yang, et al. (1999) *J. Am. Chem. Soc.* 121:4008-4018). Accordingly, the availability of chlorins with diverse substitution patterns would enable study of such electronic effects in chlorins, complementing our prior studies with porphyrins. For the construction of linear arrays, substitution at the 2- and 12-positions is quite attractive (Balasubramanian, et al. (2000) *J. Org. Chem.* 65:7919-

7929). The β-substituted Eastern and Western halves are well suited for this application. The reaction of 16 and 22-OH was performed using the previous two-flask procedure, affording chlorin 23 in 7.8% yield (Scheme 7). $^1$H NMR spectroscopy confirmed the expected structure. The geminal dimethyl groups of 23 resonate as a singlet at δ 1.97, and the CH$_2$ in the reduced pyrrole ring gives rise to a singlet downfield at δ 4.51. The four β-pyrrole hydrogens resonate in the region of δ 8.56-8.81. The eight hydrogens of the aryl rings in the β-substituents of the chlorin resonate in the region of δ 7.82-8.14 as two pairs of doublets.

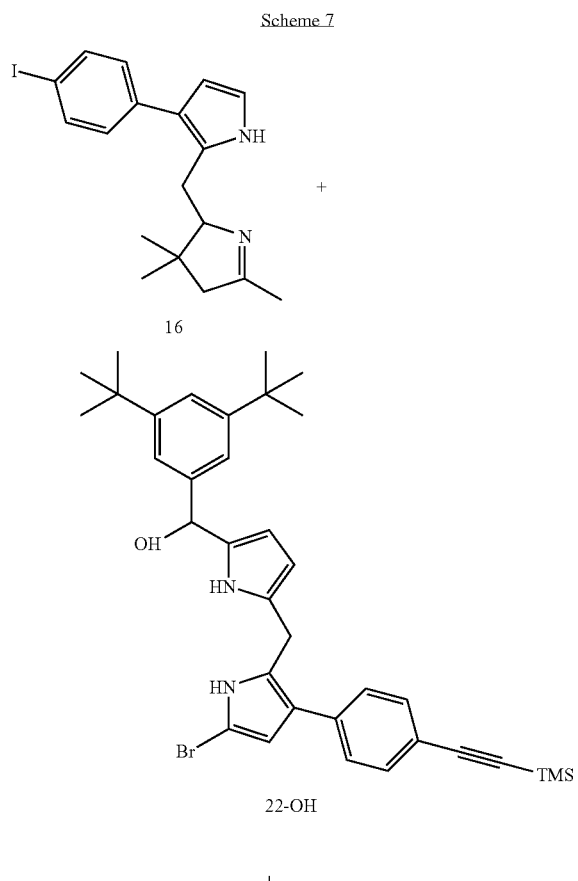

Scheme 7

General Experimental Methods.

$^1$H and $^{13}$C NMR spectra (300 MHz) were collected in CDCl$_3$ unless noted otherwise. Absorption spectra (Cary 3, 0.25 nm data intervals) were obtained at room temperature. Chlorins were analyzed by laser desorption mass spectrometry (LD-MS) in the absence of a matrix (Fenyo, et al. (1997) *J. Porphyrins Phthalocyanines* 1:93-99; Srinivasan et al. (1999) *J. Porphyrins Phthalocyanines* 3:283-291). Pyrrole was distilled at atmospheric pressure from CaH$_2$. Melting points are uncorrected. p-Iodobenzaldehyde was obtained from Karl Industries, Inc. All other reagents and starting materials were obtained from Aldrich. Chromatography was performed using flash silica (Baker) or alumina (Fisher A540, 80-200 mesh).

Solvents. THF was distilled from sodium benzophenone ketyl. Toluene was distilled from CaH$_2$. CH$_2$Cl$_2$ was distilled from CaH$_2$. The CH$_2$Cl$_2$ employed for extraction in the chlorin synthesis was distilled from CaH$_2$ and shaken with anhydrous Na$_2$CO$_3$ prior to use. CH$_3$CN (Fisher certified A.C.S.) was distilled from CaH$_2$ and stored over powdered molecular sieves. Nitromethane was stored over CaCl$_2$. Anhydrous methanol was obtained as follows. Methanol received was dried over CaH$_2$ for 12 h, and then was distilled. Other solvents were used as received.

Non-commercial compounds. The compounds 14 (Balasubramanian, et al. (2000) *J. Org. Chem.* 65:7919-7929) and 18 (Balasubramanian and Lindsey (1999) *Tetrahedron* 55:6771-6784) were prepared as described in the literature.

1,3,3-Trimethyl-7-(4-iodophenyl)-2,3,4,5-tetrahydrodipyrrin N$^{10}$-oxide (15). A solution of 1-[3-(4-iodophenyl)pyrro-2-yl]-2-nitro-3,3-dimethyl-5-hexanone (14) (0.50 g, 1.14 mmol) in acetic acid (10 mL) was treated with zinc dust (1.74 g, 26.47 mmol) all-at-once and the mixture was stirred vigorously for 1 h at room temperature. The crude reaction mixture was filtered (Celite) and concentrated. The residue was dissolved in CH$_2$Cl$_2$, washed (10% aq Na$_2$CO$_3$), dried (Na$_2$SO$_4$) and evaporated to afford a yellow solid. Recrystallization from ethyl acetate gave a white powder (200 mg, 43% yield): mp 173-174° C.; $^1$H NMR δ 0.98 (s, 3H), 1.17 (s, 3H), 2.10 (s, 3H), 2.36 (d, J=17.4 Hz, 1H), 2.52 (d, J=17.4 Hz, 1H), 3.07 (m, 2H), 3.96 (m, 1H), 6.20 (m, 1H), 6.74 (m, 1H), 7.08 (d, J=7.8 Hz, 2H), 7.67 (d, J=7.8 Hz, 2H), 11.31 (br, 1H); $^{13}$C NMR δ 13.2, 22.7, 23.5, 26.8, 37.8, 46.8, 81.0, 90.1, 107.8, 117.0, 120.6, 125.7, 130.2, 137.0, 137.3, 145.5; Anal. Calcd. for C$_{18}$H$_{21}$NIO$_2$: C, 52.95; H, 5.18; N, 6.86. Found: C, 52.91; H, 5.23; N, 6.78.

1,3,3-Trimethyl-7-(4-iodophenyl)-2,3,4,5-tetrahydrodipyrrin (16). Following a procedure for the deoxygenation of N-oxides (EXAMPLE 1), TiCl$_4$ (1.0 mL, 8.8 mmol) was slowly added to a stirred solution of dry THF (20 mL) under argon at 0° C. To the resulting yellow solution, LiAlH$_4$ (223 mg, 5.9 mmol) was added slowly and the black mixture was stirred at room temperature for 15 min, then triethylamine (7.7 mL) was added. The black mixture was then poured into a solution of 15 (500 mg, 1.22 mmol) in THF (20 mL). The mixture was stirred for 2 h at room temperature and then water (20 mL) was added. The mixture was filtered to remove inorganic materials. The filtrate was extracted (CH$_2$Cl$_2$). The organic layer was dried (Na$_2$SO$_4$) and evaporated under reduced pressure. The resulting brown oil was purified by chromatography (silica, ethyl acetate) to give a light brown oil which solidified on cooling (180 mg, 38%): mp 90-91° C.; $^1$H NMR δ 0.92 (s, 3H), 1.08 (s, 3H), 2.05 (s, 3H), 2.34 (m, 2H), 2.59 (m, 1H), 2.92 (m, 1H), 3.64 (d, J=11.7 Hz, 1H), 6.25 (m, 1H), 6.73 (m, 1H), 7.13 (d, J=6.6 Hz, 2H), 7.66 (d, J=6.6 Hz, 2H), 10.30 (br, 1H); $^{13}$C NMR δ 21.2, 23.5, 27.0, 27.8, 42.6, 54.9, 80.5, 90.4, 108.4, 117.0, 120.3, 128.9, 130.6, 137.8, 137.9, 175.3; FAB-MS obsd 393.0841, calcd exact mass 393.0828 (C$_{18}$H$_{21}$IN$_2$).

1,3,3-Trimethyl-7-[4-[2-(trimethylsilyl)ethynyl]phenyl]-2,3,4,5-tetrahydrodipyrrin (17). Samples of 16 (450 mg, 1.15 mmol), Pd$_2$(dba)$_3$ (81 mg, 0.09 mmol), Ph$_3$As (219 mg, 0.72 mmol), and CuI (17 mg, 0.09 mmol) were added to a 50 mL Schlenk flask. The flask was evacuated and purged with argon three times. Then deaerated anhydrous THF/triethylamine (12 mL, 1:1) was added followed by (trimethylsilyl)acetylene (243 μL, 1.72 mmol). The flask was sealed, immersed in an oil bath (37° C.), and the mixture was stirred overnight. Then CH$_2$Cl$_2$ (30 mL) was added and the mixture was filtered (Celite) and washed (CH$_2$Cl$_2$). The filtrate was concentrated. The resulting residue was purified by flash chromatography (silica, ethyl acetate) to afford a dark brown viscous oil (316 mg, 76%): $^1$H NMR δ 0.25 (s, 9H), 0.92 (s, 3H), 1.07 (s, 3H), 2.05 (s, 3H), 2.34 (m, 2H), 2.61 (m, 1H), 2.96 (m, 1H), 3.65 (d, J=11.7 Hz, 1H), 6.29 (m, 1H), 6.74 (m, 1H), 7.32 (d, J=7.8 Hz, 2H), 7.47 (d, J=7.8 Hz, 2H), 10.27 (br, 1H); $^{13}$C NMR δ 0.7, 21.1, 23.5, 27.1, 27.7, 42.6, 54.8, 80.5, 94.1, 106.3, 108.4, 117.0, 119.8, 120.9, 128.3, 129.3, 132.7, 138.7, 175.4; FAB-MS obsd 363.2271, calcd exact mass 363.2257 (C$_{23}$H$_{30}$N$_2$Si).

3-(4-Iodophenyl)-9-(3,5-di-tert-butylbenzoyl)-10-N-(tert-butoxycarbonyl)-dipyrromethane (19). A solution of 18 (896 mg, 2.0 mmol) in anhydrous THF (30 mL) under argon at 0° C. was treated slowly with EtMgBr (1M in THF, 6 mL, 6.0 mmol). The mixture was stirred for 10 min at 0° C. Then a solution of 3,5-di-tert-butylbenzoyl chloride (760 mg, 3.0 mmol) in anhydrous THF (5 mL) was added slowly and stirring was continued for 1.5 h at 0° C. The reaction was quenched with saturated aqueous NH$_4$Cl and extracted (CH$_2$Cl$_2$). The combined organic layers were washed with water and brine, dried (Na$_2$SO$_4$), and concentrated. The product was purified by flash column chromatography [silica, hexanes/ethyl acetate (4:1)] to yield a brown viscous oil which was cooled overnight in the refrigerator. A minimum amount of hexanes was added followed by sonication, affording a white solid (598 mg, 45%): mp 178-179° C; $^1$H NMR δ 1.35 (s, 18H), 1.58 (s, 9H), 4.30 (s,2H), 5.97 (m, 1H), 6.26 (m, 1H), 6.73 (m, 1H), 7.11 (d, J=6.6 Hz, 2H), 7.30 (m, 1H), 7.60 (m, 1H), 7.70 (m, 2H), 7.72(m, 2H), 9.92 (br, 1H); $^{13}$C NMR δ 25.8, 28.5, 32.0, 35.6, 85.5, 93.0, 110.1, 112.3, 120.4, 122.1, 123.9, 126.3, 127.1, 128.2, 131.2, 131.3, 135.4, 138.2, 138.6, 139.2, 150.5, 151.3, 185.7; Anal. Calcd for C$_{35}$H$_{41}$IN$_2$O$_3$: C, 63.25; H, 6.22; N, 4.21. Found: C, 64.03; H, 6.35; N, 4.15.

3-(4-Iodophenyl)-9-(3,5-di-tert-butylbenzoyl)dipyrromethane (20). A solution of 19 (600 mg, 0.90 mmol) in anhydrous THF (10 mL) under argon at room temperature was treated with methanolic NaOMe (146 mg, 2.70 mmol, in 1.0 mL of anhydrous methanol). After 10 min, the reaction was quenched with a mixture of hexanes and water (20 mL, 1:1) and extracted with ethyl acetate. The combined organic layers were washed with water and brine, dried (Na$_2$SO$_4$), and concentrated. The residue was recrystallized from ethanol to give a pale brown solid (430 mg, 84%): mp 202-203° C.; $^1$H NMR δ 1.30 (s, 18H), 4.18 (s, 2H), 6.23 (m, 2H), 6.48 (m, 1H), 6.93 (m, 1H), 7.25 (d, J=8.1 Hz, 2H),7.68 (m, 1H), 7.75 (m, 4H), 10.23 (br, 1H), 11.85 (br, 1H); $^{13}$C NMR δ 25.6, 31.9, 35.6, 91.1, 109.0, 111.2, 118.1, 121.6, 124.0, 124.2, 124.8, 127.0, 130.9, 131.5, 137.3, 138.0, 138.2, 141.5, 151.8, 187.5; Anal. Calcd for C$_{30}$H$_{33}$IN$_2$O: C, 63.83; H, 5.89; N, 4.96. Found: C, 63.74; H, 6.09; N, 5.00.

3-[4-[2-Trimethylsilyl)ethynyl]phenyl]-9-(3,5-di-tert-butylbenzoyl)dipyrromethane (21). Samples of 20 (1.0 g, 1.77 mmol), Pd$_2$(dba)$_3$ (125 mg, 0.14 mmol), Ph$_3$As (334 mg, 1.09 mmol), and CuI (26 mg, 0.14 mmol) were added to a 50 mL Schlenk flask. The flask was evacuated and purged with argon three times. Then deaerated anhydrous THF/triethylamine (18 mL, 1:1) was added followed by (trimethylsilyl)acetylene (376 μL, 2.66 mmol). The flask was sealed, immersed in an oil bath (37° C.), and the mixture was stirred overnight (16-18 h). Then CH$_2$Cl$_2$ (30 mL) was added and the mixture was filtered (Celite) and washed (CH$_2$Cl$_2$). The filtrate was concentrated. The resulting residue was purified by flash chromatography [silica, hexanes/ethyl acetate (3:1)] to afford a yellow oil which solidified on cooling (780 mg, 82%): mp 126-127° C.; $^1$H NMR δ 0.26 (s, 9H), 1.27 (s, 18H), 4.20 (s, 2H), 6.20 (m, 2H), 6.44 (m,1H), 6.87 (m, 1H), 7.40 (d, J=8.1 Hz, 2H), 7.50 (d, J=8.1 Hz, 2H), 7.64 (m, 1H), 7.72 (m, 2H), 10.14 (br, 1H), 11.73 (br, 1H); $^{13}$C NMR δ 0.7, 25.7, 31.9, 35.5, 94.4, 106.2, 109.1, 111.1, 118.1, 120.4, 122.0, 123.9, 124.1, 124.9, 126.9, 128.5, 131.5, 132.7, 138.1, 138.2, 141.3, 151.7, 187.45; Anal. Calcd for C$_{28}$H$_{28}$N$_2$OSi: C, 78.60; H, 7.92; N, 5.24. Found: C, 78.09; H, 8.03; N, 5.13.

1-Bromo-3-[4-[2-(trimethylsilyl)ethynyl]phenyl]-9-(3,5-di-tert-butylbenzoyl)-dipyrromethane (22). A solution of 21 (100 mg, 0.19 mmol) in anhydrous THF (6 mL) was cooled to −78° C. under argon. Recrystallized NBS (33 mg 0Q.19 mmol) was added and the reaction mixture was stirred for 1 h (−78° C.), then the mixture was quenched with a mixture of hexanes and water (20 mL, 1:1) and allowed to warm to 0° C. The aqueous portion was extracted with anhydrous ether and the combined organic layers were dried (K$_2$CO$_3$). The solvent was evaporated under vacuum without heating. Purification by flash chromatography [silica, hexanes/ether (2:1)] afforded a pale yellow solid (83 mg, 72%): mp 163-165° C. (dec.); $^1$H NMR δ 0.27 (s, 9H), 1.30 (s, 18H), 4.20 (s, 2H), 6.08 (m, 1H), 6.23 (m, 1H), 6.94 (m, 1H), 7.36 (d, J=7.8 Hz, 2H), 7.52 (d, J=7.8 Hz, 2H), 7.66 (s, 1H), 7.74 (s, 2H), 10.75 (br, 1H), 12.14 (br, 1H); $^{13}$C NMR δ 0.7, 24.8, 31.2, 34.9, 94.0, 97.9, 105.2, 110.0, 110.7, 120.3, 123.1, 123.7, 123.8, 125.5, 126.5, 127.9, 130.8, 132.0, 136.3, 137.3, 140.5, 151.1, 187.3; Anal. Calcd for C$_{35}$H$_{41}$BrN$_2$OSi: C, 68.50; H, 6.73; N, 4.56. Found: C, 68.06; H, 6.64; N, 4.49; FAB-MS obsd 612.2184, calcd exact mass 612.2172 (C$_{35}$H$_{41}$BrN$_2$OSi).

Zn(II)-17,18-Dihydro-18,18-dimethyl-2-(4-iodophenyl)-5-(3,5-di-tert-butylbenzoyl)-12-[4-[2-(trimethylsilyl)ethynyl]phenyl]porphyrin (23). Following the two-flask procedure (EXAMPLE 1), to a solution of 22 (123 mg, 0.20 mmol) in anhydrous THF/methanol (7.5 mL, 4:1) was added excess NaBH4 (100 mg, 2.60 mmol) in small portions at room temperature. The reaction was monitored by TLC [alumina, hexanes/ethyl acetate (1:1)]. Upon completion, the reaction mixture was quenched with cold water (10 mL), then extracted with distilled CH$_2$Cl$_2$ (3×25 mL). The combined organic layers were washed with brine (50 mL), dried (K$_2$CO$_3$) and concentrated in vacuo without heating to leave the resulting carbinol 22-OH in ~1-2 mL of CH$_2$Cl$_2$. A solution of 1,3,3-trimethyl-7-(4-iodophenyl)-2,3,4,5-tetrahydrodipyrrin (16) (78 mg, 0.20 mmol) in a few milliliters of anhydrous CH$_3$CN was combined with the carbinol, then additional anhydrous CH$_3$CN was added to give a total of 20 mL of CH$_3$CN. The solution was stirred at room temperature under argon and TFA (20 μL, 0.26 mmol) was added. The reaction was monitored by TLC [alumina, hexanes/ethyl acetate (3:1)]; after 1 h the carbinol had disappeared. The reaction mixture was quenched with 10% aqueous NaHCO$_3$ and extracted with distilled CH$_2$Cl$_2$ (3×25 mL). The combined organic layers were washed with water and brine, then dried (Na$_2$SO$_4$). The solvent was removed in vacuo at room temperature. The residue was dissolved in 14, mL of anhydrous toluene under argon, then AgIO$_3$ (848 mg, 3.0 mmol), piperidine (300 μL, 3.0 mmol) and Zn(OAc)$_2$ (550 mg, 3.0 mmol) were added. The resulting mixture was heated at 80° C. for 3 h. The reaction was monitored by TLC [silica, hexanes/CH$_2$Cl$_2$ (1:1); showing a single green spot]. The mixture was cooled to room temperature, then passed through a short column (silica, CH$_2$Cl$_2$). The major fraction was concentrated and again chromatographed [silica, hexanes/CH$_2$Cl$_2$ (2:1 then 1:1)] to give a greenish blue solid (15 mg, 7.8%): $^1$H NMR δ 0.35 (s, 9H), 1.51 (s, 18H), 1.97 (s, 6H), 4.51 (s, 2H), 7.42 (s, 1H), 7.82 (d, J=9.0 Hz, 2H), 7.87 (d, J=7.8 Hz, 2H), 7.96 (m, 2H), 8.03 (d, J=8.1 Hz, 2H), 8.14 (d, J=8.1 Hz, 2H), 8.56 (d, J=4.5 Hz, 1H), 8.66 (m, 2H), 8.72 (m, 2H), 8.81 (d, J=4.5 Hz, 1H), 9.61 (s, 1H); LD-MS obsd 964.60; FAB-MS obsd 964.2382, calcd exact mass 964.2376 (C$_{53}$H$_{53}$IN$_4$SiZn); λ$_{abs}$ (toluene)/nm 417 (log ε=5.30, fwhm=20 nm), 629 (4.86); λ$_{em}$ 634, 691 nm.

Conclusions. We have developed a tetrahydrodipyrrin Western half for the synthesis of chlorin building blocks. The new Western Half is obtained via the reductive cyclization of a nitro-hexanone substituted pyrrole followed by mild deoxygenation with a Ti(0) reagent. The tetrahydrodipyrrin is more stable than the dihydrodipyrrin used previously. The facile condensation of the Eastern half and Western half is performed at room temperature for a few minutes. The oxidative cyclization is performed at 80° C. for several hours in the presence of a zinc template. The tetrahydrobilene-α formed in the condensation of the Eastern and Western halves has been isolated and found to be reasonably stable. A one-flask synthetic procedure for chlorin formation has been developed. Several zinc chlorins were synthesized, with yields of 9 to 19% in the ring-forming step.

EXAMPLE 3

Isolation and Characterization of a 2-iodo-chlorin Byproduct

During our initial synthesis of a chlorin using the tetrahydrodipyrrin Western half, we employed the condensation and oxidation conditions (Strachan, et al. (2000) *J. Org. Chem.* 65:3160-3172) developed for the dipyrrin Western half. Thus, a reaction was performed of 4 and an iodo-phenyl substituted Eastern half (6g-OH) in acetonitrile containing 10 mM TFA followed by oxidative cyclization using AgIO$_3$, Zn(OAc)$_2$, and piperidine in toluene at 80° C. (Scheme 8). In addition to the desired chlorin (Zn-8h), we identified a byproduct upon examination of the LD-MS spectrum. The LD-MS spectrum shows peaks at m/z=694 and 820, the former of which corresponds to the desired chlorin Zn-8h. This Δm of 126 is ascribed to the presence of an iodo atom (note that the chlorin target molecule bears a single iodo group; the byproduct bears two iodo groups). However, only a single chlorin spot was observed upon TLC analysis. The absorption spectrum in the Q$_y$(0,0) region was somewhat broad. Upon demetalation of the zinc-chlorin material, TLC analysis showed the presence of two chlorin species. Isolation and characterization (particularly with $^1$H NMR and NOE experiments) revealed that the iodination occurred regiospecifically at the 2-position. We note that this iodinated byproduct may have useful synthetic applications. The following experimental section describes the isolation and characterization data for the 2-iodo-chlorin byproduct.

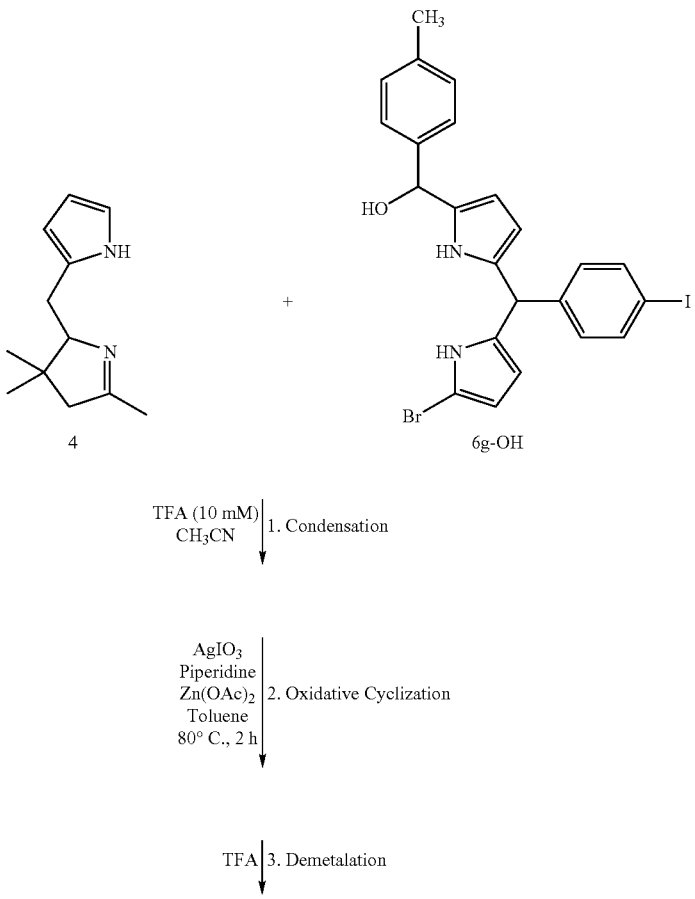

Scheme 8

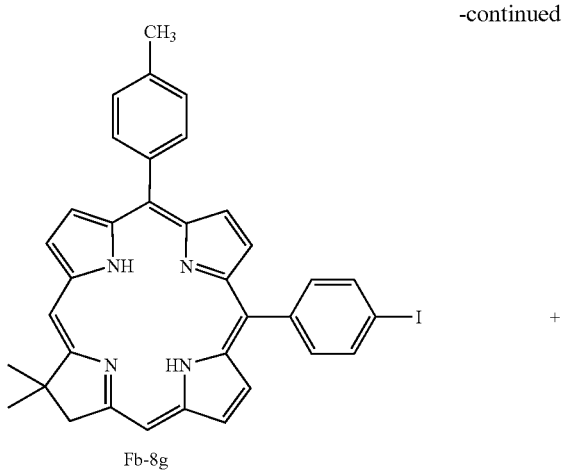

Fb-8g

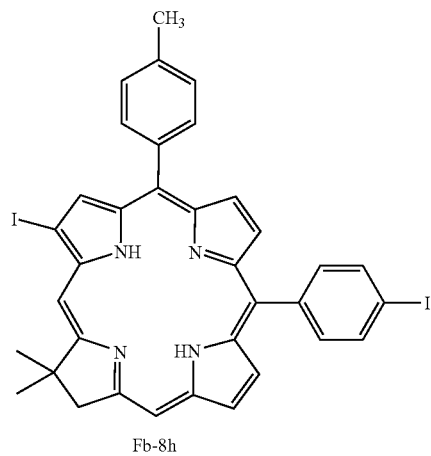

Fb-8h

Synthesis of 17,18-dihydro-18,18-dimethyl-5-(4-methylphenyl)-10-(4-iodophenyl)-porphyrin (Fb-8g) and 17,18-dihydro-18,18-dimethyl-5-(4-methylphenyl)-2-iodo-10-(4-iodophenyl)porphyrin (Fb-8h). Following the general procedure, treatment of 6g (272 mg, 0.500 mmol) with NaBH$_4$ (114 mg, 3.01 mmol) in 7.5 mL of anhydrous THF/methanol (4:1) afforded 6g-OH. The residue was dissolved in 50 mL of anhydrous CH$_3$CN. 1,3,3-trimethyl-2,3,4,5-tetrahydrodipyrrin (4, 100 mg, 0.530 mmol) was added following TFA (38 μL, 0.50 mmol, 10 mM). The solution was stirred at room temperature for 30 min. The reaction was quenched with 10% aqueous NaHCO$_3$ (50 mL) and extracted with distilled CH$_2$CL$_2$ (3×50 mL). The combined organic layers were washed with water, dried (Na$_2$CO$_3$) and concentrated in vacuo without heating. The residue was dissolved in 50 mL of toluene, to which AgIO$_3$ (2.12 g, 7.50 mmol), Zn(OAc)$_2$ (1.38 g, 7.50 mmol) and piperidine (740 μL, 7.50 mmol) were added. The reaction mixture was heated at 80° C. exposed to air for 2 h. The reaction mixture was concentrated under reduced pressure. The residue was passed through a short silica gel column eluting with CH$_2$Cl$_2$. The major fraction was concentrated and again chromatographed on silica eluting with hexanes/CH$_2$Cl$_2$ (2:1) to afford a blue solid (66 mg). From the blue solid, 56 mg was taken and dissolved in 10 mL of CH$_2$Cl$_2$ and treated with TFA (310 μL, 4.04 mmol). The demetalation was complete in 1 h as confirmed by UV-Vis and TLC analyses. Then 70 mL of CH$_2$Cl$_2$ and 2 mL of triethylamine were added to the reaction mixture. The mixture was washed with saturated aqueous NaHCO$_3$ (100 mL×2) and dried (Na$_2$SO$_4$). TLC analysis [silica, hexanes/CH$_2$Cl$_2$ (1:1)] showed two components: a former component ($R_f$=0.72; Fb-8h) and a latter component ($R_f$=0.57; Fb-8g). The solvent was removed under vacuum. Chromatography of the residue [silica, hexanes/CH$_2$Cl$_2$ (3:1)] afforded Fb-8g (32 mg, 12%) and Fb-8h (19 mg, 6%). Analytical data of Fb-8g are consistent with the literature values (Strachan, et al. (2000) *J. Org. Chem.* 65:3160-3172). Fb-8h: $^1$H NMR 6-1.66 (bs, 2H), 2.07 (s, 6H), 2.67 (s, 3H), 4.58 (s, 2H), 7.51 (d, J=8.1 Hz, 2H), 7.82 (d J=8.1 Hz, 2H), 7.96 (d, J=8.1 Hz, 2H), 8.03 (d J=8.1 Hz, 2H), 8.40 (d, J=4.4 Hz, 1H), 8.48 (d, J=4.4 Hz, 1H), 8.70 (d, J=4.4 Hz, 1H), 8.77 (d, J=4.4 Hz, 1H), 8.88 (s, 1H), 8.95 (s, 1H), 8.97 (s, 1H); LD-MS obsd 757.24; FAB-MS obsd 759.0480, calcd 759.0482 (C$_{35}$H$_{28}$I$_2$N$_4$); $\lambda_{abs}$ (toluene) 420, 512, 649 nm.

The foregoing is illustrative of the present invention, and is not to be construed as limiting thereof. The invention is defined by the following claims, with equivalents of the claims to be included therein.

What is claimed is:
1. A method of making a tetrahydrobilene of Formula XI:

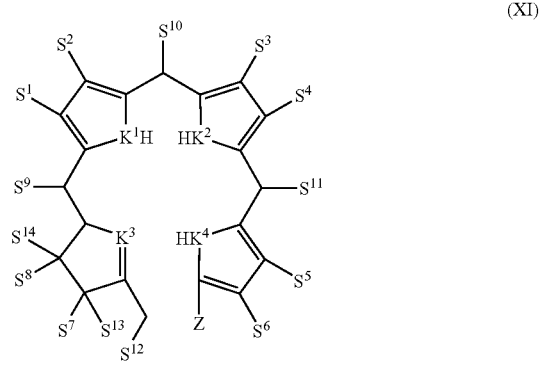

(XI)

wherein:
K$^1$, K$^2$ and K$^4$ are hetero atoms independently selected from the group consisting of NH, O, S, Se, Te, and CH$_2$;
K$^3$ is N;
S$^1$, S$^2$, S$^3$, S$^4$, S$^5$, S$^6$, S$^7$, S$^8$, S$^9$, S$^{10}$, S$^{11}$, S$^{12}$, S$^{13}$, and S$^{14}$ are independently selected from the group consisting of H, aryl, phenyl, cycloalkyl, alkyl, alkenyl, alkynyl, halogen, alkoxy, alkylthio, perfluoroalkyl, perfluoroaryl, pyridyl, cyano, thiocyanato, nitro, amino, alkylamino, acyl, sulfoxyl, sulfonyl, imido, amido, and carbamoyl;
and wherein from one to four of S$^1$, S$^2$, S$^3$, S$^4$, S$^5$, S$^6$, S$^7$, S$^8$, S$^9$, S$^{10}$, S$^{11}$, S$^{12}$, S$^{13}$, and S$^{14}$ may optionally be independently selected linking groups Q, wherein said linking groups Q are of the formula:

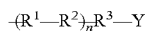

wherein;
n is from 0 to 10;
R$^3$ may be present or absent;
R$^1$, R$^2$, and R$^3$ are each independently selected from the group consisting of ethene, ethyne, aryl, and heteroaryl groups, which aryl and heteroaryl groups may be unsubstituted or substituted one or more times with H, aryl, phenyl, cycloalkyl, alkyl, alkenyl, alkynyl, halogen, alkoxy, alkylthio, perfluoroalkyl, perfluoroaryl, pyridyl, cyano, thiocyanato, nitro, amino, alkylamino, acyl, sulfoxyl, sulfonyl, imido, amido, and carbamoyl;

Y is a protected or unprotected reactive substituent selected from the group consisting of hydroxy, thio, seleno, telluro, ester, carboxylic acid, boronic acid, phenol, silane, sulfonic acid, phosphonic acid, alkylthiol, formyl, halo, alkenyl, alkynyl, haloalkyl, alkyl phosphonate, alkyl sulfonate, alkyl carboxylate, and alkyl boronate groups; and Z is selected from the group consisting of halo, alkoxy, and acyloxy;

said method comprising condensing a compound of Formula WH with a compound of Formula EH

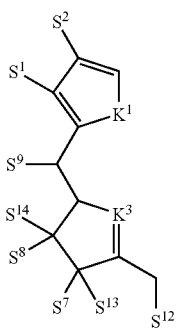

WH

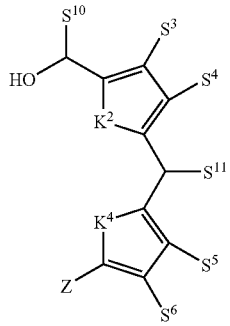

EH in an organic solvent in the presence of an acid to form a tetrahydrobilene of Formula XI.

2. The method according to claim 1, wherein said acid is a Bronsted or Lewis acid.

3. The method according to claim 1, wherein said acid is trifluoroacetic acid.

4. The method according to claim 1, wherein said condensing step is carried out under nonaqueous conditions.

5. The method according to claim 1, wherein said organic solvent is a polar or nonpolar aprotic solvent.

6. The method according to claim 1, wherein said organic solvent is acetonitrile, tetrahydrofuran or a mixture thereof.

* * * * *

UNITED STATES PATENT AND TRADEMARK OFFICE
CERTIFICATE OF CORRECTION

PATENT NO. : 7,470,785 B2
APPLICATION NO. : 11/072196
DATED : December 30, 2008
INVENTOR(S) : Lindsey et al.

Page 1 of 1

It is certified that error appears in the above-identified patent and that said Letters Patent is hereby corrected as shown below:

Column 48, Claim 1, Lines 30-45: Please correct Formula XI:

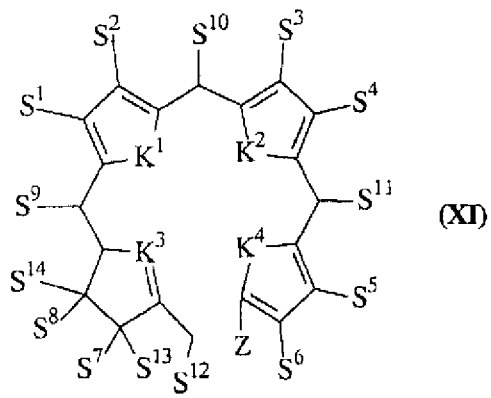

(XI)

Signed and Sealed this

Twenty-fourth Day of March, 2009

JOHN DOLL
*Acting Director of the United States Patent and Trademark Office*